(12) United States Patent
Freeman et al.

(10) Patent No.: US 9,457,080 B2
(45) Date of Patent: Oct. 4, 2016

(54) METHODS AND COMPOSITIONS FOR THE TREATMENT OF PERSISTENT INFECTIONS AND CANCER BY INHIBITING THE PROGRAMMED CELL DEATH 1 (PD-1) PATHWAY

(71) Applicants: Emory University, Atlanta, GA (US); Dana-Farber Cancer Institute, Inc., Boston, MA (US); Brigham and Women's Hospital, Boston, MA (US); President and Fellows of Harvard College, Cambridge, MA (US)

(72) Inventors: Gordon Freeman, Brookline, MA (US); Arlene Sharpe, Brookline, MA (US); David M. Dorfman, Brookline, MA (US); Rafi Ahmed, Atlanta, GA (US); Daniel Barber, Rockville, MD (US); E. John Wherry, Havertown, PA (US)

(73) Assignees: Emory University, Atlanta, GA (US); Dana-Farber Cancer Institute, Inc., Boston, MA (US); Brigham and Women's Hospital, Inc., Boston, MA (US); President and Fellows of Harvard College, Cambridge, MA (US)

( * ) Notice: Subject to any disclaimer, the term of this patent is extended or adjusted under 35 U.S.C. 154(b) by 132 days.

(21) Appl. No.: 14/144,304

(22) Filed: Dec. 30, 2013

(65) Prior Publication Data

US 2014/0178370 A1      Jun. 26, 2014

Related U.S. Application Data

(63) Continuation of application No. 11/449,919, filed on Jun. 8, 2006, now Pat. No. 8,652,465.

(60) Provisional application No. 60/688,872, filed on Jun. 8, 2005.

(51) Int. Cl.

| | |
|---|---|
| *A61K 39/395* | (2006.01) |
| *C07K 16/28* | (2006.01) |
| *A61K 38/17* | (2006.01) |
| *G01N 33/50* | (2006.01) |
| *G01N 33/574* | (2006.01) |
| *A61K 31/713* | (2006.01) |
| *A61K 39/39* | (2006.01) |
| *C12N 15/113* | (2010.01) |
| *A61K 39/00* | (2006.01) |

(52) U.S. Cl.
CPC ....... *A61K 39/39558* (2013.01); *A61K 31/713* (2013.01); *A61K 38/1709* (2013.01); *A61K 39/39* (2013.01); *C07K 16/2803* (2013.01); *C07K 16/2818* (2013.01); *C07K 16/2827* (2013.01); *C12N 15/1138* (2013.01); *G01N 33/505* (2013.01); *G01N 33/5011* (2013.01); *G01N 33/57484* (2013.01); *A61K 2039/505* (2013.01); *C07K 2317/74* (2013.01); *C07K 2317/76* (2013.01); *G01N 2800/26* (2013.01)

(58) Field of Classification Search
None
See application file for complete search history.

(56) References Cited

U.S. PATENT DOCUMENTS

| | | |
|---|---|---|
| 5,698,520 A | 12/1997 | Honjo et al. |
| 5,858,358 A | 1/1999 | June et al. |
| 5,939,281 A | 8/1999 | Lehmann et al. |
| 6,103,479 A | 8/2000 | Taylor |
| 6,232,445 B1 | 5/2001 | Rhode et al. |
| 6,235,488 B1 | 5/2001 | Tom-Moy et al. |
| 6,329,209 B1 | 12/2001 | Wagner et al. |
| 6,355,479 B1 | 3/2002 | Webb et al. |
| 6,610,542 B1 | 8/2003 | Bell et al. |
| 6,803,192 B1 | 10/2004 | Chen |
| 6,808,710 B1 | 10/2004 | Wood et al. |
| 6,913,747 B1 | 7/2005 | Co et al. |
| 6,936,704 B1 | 8/2005 | Freeman et al. |
| 6,984,720 B1 | 1/2006 | Korman et al. |
| 7,041,474 B2 | 5/2006 | Kingsbury |
| 7,101,550 B2 | 9/2006 | Wood et al. |
| 7,105,328 B2 | 9/2006 | Wood et al. |
| 7,195,798 B2 | 3/2007 | Wung et al. |
| 7,238,360 B2 | 7/2007 | Shirwan |
| 7,385,036 B2 | 6/2008 | Kingsbury |
| 7,432,059 B2 | 10/2008 | Freeman et al. |
| 2002/0095024 A1 | 7/2002 | Mikesell et al. |
| 2002/0099022 A1 | 7/2002 | Killam |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0160000 A1 | 10/2002 | Wood et al. |
| 2002/0164600 A1 | 11/2002 | Freeman et al. |

(Continued)

FOREIGN PATENT DOCUMENTS

| | | |
|---|---|---|
| EP | 0 670 369 A2 | 9/1995 |
| EP | 1 074 617 A2 | 2/2001 |

(Continued)

OTHER PUBLICATIONS

Leung et al., Immune Network 2014, 14: 265-276.*

(Continued)

*Primary Examiner* — Ilia Ouspenski
(74) *Attorney, Agent, or Firm* — Klarquist Sparkman, LLP

(57) ABSTRACT

The present invention provides methods and compositions for the treatment, prevention, or reduction of persistent infections, such as chronic infections, latent infections, and slow infections and cancer. The methods and compositions of the invention are also useful for the alleviation of one or more symptoms associated with such infections and cancer.

16 Claims, 9 Drawing Sheets

(56) References Cited

U.S. PATENT DOCUMENTS

| | | |
|---|---|---|
| 2003/0027998 A1 | 2/2003 | Holtzman et al. |
| 2003/0039653 A1 | 2/2003 | Chen et al. |
| 2003/0044768 A1 | 3/2003 | Wood et al. |
| 2003/0064380 A1 | 4/2003 | Rao et al. |
| 2003/0118592 A1 | 6/2003 | Ledbetter et al. |
| 2003/0133939 A1 | 7/2003 | Ledbetter et al. |
| 2003/0147896 A1 | 8/2003 | Solanki |
| 2003/0161827 A1 | 8/2003 | Celnicker et al. |
| 2003/0166531 A1 | 9/2003 | Madrenas et al. |
| 2003/0180292 A1 | 9/2003 | Hanna et al. |
| 2003/0180309 A1 | 9/2003 | Baum et al. |
| 2003/0224520 A1 | 12/2003 | June et al. |
| 2003/0232323 A1 | 12/2003 | Freeman et al. |
| 2004/0101519 A1 | 5/2004 | June et al. |
| 2004/0110290 A1 | 6/2004 | June et al. |
| 2004/0137577 A1 | 7/2004 | Coyle et al. |
| 2004/0156858 A1 | 8/2004 | Franzusoff et al. |
| 2004/0180047 A1 | 9/2004 | Chen et al. |
| 2004/0248205 A1 | 12/2004 | Stern et al. |
| 2005/0136049 A1 | 6/2005 | Ledbetter et al. |
| 2005/0208496 A1 | 9/2005 | Ohtani et al. |
| 2006/0003452 A1 | 1/2006 | Humeau et al. |
| 2006/0034810 A1 | 2/2006 | Riley et al. |
| 2006/0034826 A1 | 2/2006 | Carreno |
| 2006/0052295 A1 | 3/2006 | Terman |
| 2006/0083744 A1 | 4/2006 | Chen et al. |
| 2006/0110383 A1* | 5/2006 | Honjo ............... A61K 31/7088 424/133.1 |
| 2006/0110755 A1 | 5/2006 | Duke et al. |
| 2006/0165665 A1 | 7/2006 | Min et al. |
| 2006/0205034 A1 | 9/2006 | Fraser et al. |
| 2006/0269526 A1 | 11/2006 | Galipeau et al. |
| 2006/0276422 A1 | 12/2006 | Usman et al. |
| 2007/0036783 A1 | 2/2007 | Humeau et al. |
| 2007/0122378 A1 | 5/2007 | Freeman et al. |
| 2007/0172504 A1 | 7/2007 | Shirwan et al. |
| 2007/0172947 A1 | 7/2007 | Shirwan |
| 2007/0184473 A1 | 8/2007 | Shirwan et al. |
| 2007/0243584 A1 | 10/2007 | West |
| 2008/0069831 A1 | 3/2008 | Duke et al. |
| 2008/0069833 A1 | 3/2008 | Franzusoff et al. |
| 2008/0107671 A1 | 5/2008 | Duke et al. |
| 2008/0118511 A1 | 5/2008 | Freeman et al. |
| 2009/0055944 A1* | 2/2009 | Korman ............. C07K 16/2827 800/18 |
| 2009/0217401 A1* | 8/2009 | Korman ................ C07K 16/18 800/18 |
| 2010/0040614 A1 | 2/2010 | Ahmed et al. |
| 2010/0151492 A1 | 6/2010 | Ahmed et al. |
| 2012/0251537 A1 | 10/2012 | Ahmed et al. |
| 2015/0239972 A1 | 8/2015 | Ahmed et al. |

FOREIGN PATENT DOCUMENTS

| | | |
|---|---|---|
| EP | 1 537 878 A1 | 6/2005 |
| EP | 1 997 887 | 9/2013 |
| JP | 2007-089496 | 4/2007 |
| WO | WO 95/03408 | 2/1995 |
| WO | WO 97/46256 | 12/1997 |
| WO | WO 00/32231 | 6/2000 |
| WO | WO 00/55375 | 9/2000 |
| WO | WO 00/61612 | 10/2000 |
| WO | WO 01/14556 A1 | 3/2001 |
| WO | WO 01/14557 A1 | 3/2001 |
| WO | WO 01/21631 A2 | 3/2001 |
| WO | WO 01/34629 A1 | 5/2001 |
| WO | WO 01/39722 A2 | 6/2001 |
| WO | WO 01/68134 A3 | 9/2001 |
| WO | WO 01/77137 A1 | 10/2001 |
| WO | WO 01/83750 A2 | 11/2001 |
| WO | WO 01/94413 A2 | 12/2001 |
| WO | WO 02/00692 A2 | 1/2002 |
| WO | WO 02/00730 | 1/2002 |
| WO | WO 02/08279 A2 | 1/2002 |
| WO | WO 02/068647 A2 | 9/2002 |
| WO | WO 02/072631 A2 | 9/2002 |
| WO | WO 02/077208 A1 | 10/2002 |
| WO | WO 02/079474 A2 | 10/2002 |
| WO | WO 02/079499 A1 | 10/2002 |
| WO | WO 02/086083 A2 | 10/2002 |
| WO | WO 2002/078731 A2 | 10/2002 |
| WO | WO 02/092792 A2 | 11/2002 |
| WO | WO 02/092793 A1 | 11/2002 |
| WO | WO 03/006632 A2 | 1/2003 |
| WO | WO 03/042402 A2 | 5/2003 |
| WO | WO 03/083069 A2 | 10/2003 |
| WO | WO 03/086459 | 10/2003 |
| WO | WO 03/104456 A1 | 12/2003 |
| WO | WO 2004/000221 A2 | 12/2003 |
| WO | WO 2004/004771 | 1/2004 |
| WO | WO 2004/037321 A2 | 5/2004 |
| WO | WO 2004/056785 | 7/2004 |
| WO | WO 2004/056875 | 7/2004 |
| WO | WO 2004/094458 A2 | 11/2004 |
| WO | WO 2005/035779 | 4/2005 |
| WO | WO 2005/042556 A1 | 5/2005 |
| WO | WO 2005/044835 A1 | 5/2005 |
| WO | WO 2005/046712 A1 | 5/2005 |
| WO | WO 2005/047288 A1 | 5/2005 |
| WO | WO 2005/042769 A1 | 12/2005 |
| WO | WO 2006/007539 A1 | 1/2006 |
| WO | WO 2006/042237 A2 | 4/2006 |
| WO | WO 2006/121168 A1 | 11/2006 |
| WO | WO 2006/133396 A2 | 12/2006 |
| WO | WO 2007/005874 A2 | 1/2007 |
| WO | WO 2007/016340 | 2/2007 |
| WO | WO 2007/030523 | 3/2007 |
| WO | WO 2007/067681 A2 | 6/2007 |
| WO | WO 2007/067682 A2 | 6/2007 |
| WO | WO 2007/067683 A2 | 6/2007 |
| WO | WO 2007/082144 A2 | 7/2007 |
| WO | WO 2007/082154 A2 | 7/2007 |
| WO | WO 2007/084865 A2 | 7/2007 |
| WO | WO 2007/100098 A1 | 9/2007 |
| WO | WO 2007/121364 A2 | 10/2007 |
| WO | WO 2007/124361 A2 | 11/2007 |
| WO | WO 2008/034076 A2 | 3/2008 |
| WO | WO 2008/078673 | 7/2008 |
| WO | WO 2008/083174 A3 | 7/2008 |
| WO | WO 2008/085562 A2 | 7/2008 |
| WO | WO 2008/091643 A2 | 7/2008 |
| WO | WO 2008/092153 A2 | 7/2008 |

OTHER PUBLICATIONS

Selenko-Gebauer et al., J Immunol 2003, 170: 3637-3644.*
Vereecque et al., Leukemia 2004, 18: 1223-1230.*
Yamazaki et al., J Immunol 2002, 169: 5538-5545.*
Yang et al., Blood 2006, 107: 3639-3646.*
Hirano et al. (Cancer Res., Feb. 1, 2005; 65(3): 1089-1096).*
Okazaki et al., Trends in Immunology (Apr. 2006), vol. 27 No. 4, p. 195-201.*
Wei et al., "Strength of PD-1 signaling differentially affects T-cell effector functions," *Proceedings of the National Academy of Sciences*, vol. 110, No. 27, published online Apr. 22, 2013, pp. E2480-E2489.
Iwai and Honjo, "Cancer cell immune escape mechanisms through PD-1/PD-L1 signals," *Genetic Medicine* 7(1):109-111 (2003) (in Japanese, with English Language Translation).
Saudemont and Quesnel, "In a model of tumor dormancy, long-term persistent leukemic cells have increased B7-H1 and B7.1 expression and resist CTL-mediated lysis," *Blood* 104:2124-2133 (2004).
Planz et al., "A critical role for neutralizing-antibody-producing B cells, CD4+T cells, and interferons in persistent and acute infections of mice with lymphocytic choriomeningitis virus: Implications for adoptive immunotherapy of virus carriers," *Proc. Natl. Acad. Sci. USA* 94:6874-6879 (Jun. 1997).
Wilson and Brooks, "Translating insights from persistent LCMV infection into anti-HIV immunity," *Immunol Res.* 48(1-3):3-13 (Dec. 2010).
Agata et al., "Expression of the PD-1 antigen on the surface of stimulated mouse T and B lymphocytes," *Int. Immunol.*, 8(5):765-772 (1996).

(56) References Cited

OTHER PUBLICATIONS

Ahmed et al. "Immune Therapy of a Persistent and Disseminated Viral Infection," *Journal of Virolgoy* 61(12):3920-3929 (1987).
Ansari et al., "The Programmed Death-1 (PD-1) Pathway Regulates Autoimmune Diabetes in Nonobese Diabetic (NOD) Mice," *J. Exp. Med.*, 198(1):63-69 (2003).
Barber et al., "PD-L1 Blockade Restores Function to CD8 T cells during Chronic Viral Infection," Experimental Biology/IUPS 2005: Meeting Abstracts *FASEB Journal* 19(4):Supple., p. A893(#551.1) (dated Mar. 4, 2005).
Barber et al., "Restoring function in exhausted CD8 T cells during chronic viral infection," *Nature*, 439(9):682-687, (Feb. 9, 2006).
Bendayan "Possibilities of False Immunocytochemical Results Generated by The Use of Monoclonal Antibodies: The Example of the Anti-proinsulin Antibody," *J Histochem. Cytochem.*, 43(9):881-886 (1995).
Blank et al., "Blockade of PD-L1 (B7-H1) Augments Human Tumor-specific T Cell Responses in Vitro," *International Journal of Cancer* 119:317-327 (2006).
Blank et al., "Interaction of PD-L1 on tumor cells with PD-1 on tumor-specific T cells as a mechanism of immune evasion: implications for tumor immunotherapy," Cancer Immunol. Immunother. 54(4):307-14(2005).
Bordignon et al., "Cell Therapy: Achievements and Perspectives," *Haematologica*, 84:1110-1149 (1999).
Borkner et al., "RNA Interface Targeting Programmed Death Receptor-1 Improves Immune Functions of Tumor-specific T cells," *Cancer Immunology Immunotherapy*, 59:1173-1183 (2010).
Branch, "A good antisense molecule is hard to find," *TIBS*, 23(2):45-50 (1998).
Britten et al., "The use of HLA-A* 0201-transfected K562 as standard antigen-presenting cells for CD8$^+$T lymphocytes in INF-β ELISPOT assays," *J Immunol. Meth.*, 259:95-110 (2002).
Brown et al., "Blockade of Programmed Death-1 Ligands on Dendritic Cells Enhances T Cell Activation and Cytokine Production[1]," *J Immunol.*, 170:1257-1266 (2003).
Browne et al., "The B-Cell Transcription Factors BSAO, Oct-2, and BOB.1 and the Pan-B-Cell Markers CD20, CD22, and CD79a Are Useful in the Differential Diagnosis of Classic Hodgkin Lymphoma," Am. J Clin. Pathol. 120:767-777 (2003).
Cai et al., "PD-1 ligands, negative regulators for activation of naïve, memory, and recently activated human CD4+ T cells," *Cellular Immunology* 230:89-98 (2004).
Coyle et al., "The expanding B7 superfamily: Increasing complexity in costimulatory signals regulating T cell function," *Nat. Immunol.*, 2(3):203-209 (2001).
Curiel et al., "Blockade of B7-H1 Improves Myeloid Dendritic Cell-Mediated Antitumor Immunity," Nature Medicine 9(5):562-567 (2003).
Day et al., "PD-1 expression on HIV-specific T cells is associated with T-cell exhaustion and disease progression," *Nature*, 443(21):350-354, (Sep. 21, 2006).
Desrosiers, "Prospects for an AIDS Vaccine," Nature Med 10(3):221-223 (2004).
Dong et al., "B7-H1, a third member of the B7 family, co-stimulates T-cell proliferation and interleukin-10 secretion," *Nat. Med.*, 5(12):1365-1369 (1999).
Ellis et al., "Interactions of CD80 and CD86 with CD28 and CTLA4," *J. Immunol.*, 156:2700-2709 (1996).
EMBL Acc No. AF142780 "Mus musculus butyrophilin-like protein (Btdc) mRNA, complete cds," (Apr. 12, 2001).
EMBL Acc No. AF329193 "Homo sapiens butyrophilin precursor B7-DC mRNA, complete cds" (Apr. 10, 2001).
EMBL Acc No. AF344424 "Homo sapiens PD-1-ligand 2 protein (PDL2) mRNA, complete cds," (Apr. 8, 2002).
EMBL Acc No. AK001872 "Homo sapiens cDNA FLJ11010 fis, clone PLACE1003145" (Jan. 9, 2008).
EMBL Acc No. AL162253 "Human DNA sequence from clone RP11-574F11 on chromosome 9 Contains the gene for B7-H1 protein (PD-L1), the gene for programmed death ligand 2 (PDL2) (PDCD1L2) and a novel gene, complete sequence" (Jan. 13, 2009).
Fanger et al., "Type I (CD64) and Type II (CD32) Fcγ Receptor-Mediated Phagocytosis by Human Blood Dendritic Cells," *J. Immunol.* 157:541-548 (1996).
Freeman et al., "Engagement of the PD-1 Immunoinhibitory Receptor by a Novel B7 Family Member Leads to Negative Regulation of Lymphocyte Activation," *Journal of Experimental Medicine* 192(7):1027-1034 (2000).
Freeman et al., "Reinvigorating exhausted HIV-specific T cells via PD-1-PD-1 ligand blockade," *JEM* 203(10): 2223-2227 (Oct. 2, 2006).
Freeman et al., "The B7-homologue, PD-L, is the ligand of the PD-1 Immunoinhibitory Receptor," FASEB J., 14(6):A1170, Abstract 153.34 (2000).
Gajewski et al., "Immune Suppression in the Tumor Microenvironment," *Journal of Immunotherapy*, 29:233-240 (2006).
GENESEQ Acc. No. AAH07485 "Golga4 protein" (Feb. 13, 2004).
GENESEQ Acc. No. AAH14818 "NADH dehydrogenase (ubiquinone) flavoprotein 1" (Dec. 2, 2006).
Ghiotto et al., "PD-L1 and PD-L2 differ in their molecular mechanisms of interaction with PD-1," *International Immunology* 22(8): 651-660 (Jun. 29, 2010).
Giorgi et al., "Elevated Levels of CD38$^+$CD8$^+$T Cells in HIV Infection Add to the Prognostic Value of Low CD4$^+$T Cell Levels: Results of 6 Years of Follow-Up," *Journal of Acquired Immune Deficiency Syndromes*, 6:904-912 (1993).
Greenfield et al., "CD28/B7 Costimulation: A Review," *Crit. Rev. Immunol.*, 18:389-418 (1998).
Greenwald et al., "Negative co-receptors on lymphocytes," *Curr. Opin. Immunol.*, 14:391-396 (2002).
Ha et al., "Enhancing therapeutic vaccination by blocking PD-1-mediated inhibitory signals during chronic infection," *J. Exp. Med.* 205(3): 543-554 (2008).
Haibricht et al., "Striking dichotomy of PD-L1 and PD-L2 pathways in regulating alloreactive CD4$^+$and CD8$^+$T cells in vivo," *T Am. J. Transplan.* 7: 2683-2692 (2007).
Haynes and Montefiori, "Aiming to induce broadly reactive neutralizing antibody responses with HIV-1 vaccine candidates," *Expert Rev Vaccines* 5(3): 347-363 (2006).
Haynes and Shattock, "Critical Issued in Mucosal Immunity for HIV-1 Vaccine Development," J. Allergy Clin. Immunol. 122:3-9 (2008).
He et al., "Blockade of B7-H1 with sPD-1 improves immunity against murine hepatocarcinoma," *Anticancer Res.*, 25(5):3309-13 (2005).
Henry et al., "Structure and evolution of the extended B7 family, " *Immunol. Today*, 20(6):285-288 (1999).
Hirano et al., "Blockade of B7-H1 and PD-1 by monoclonal antibodies potentiates cancer therapeutic immunity," *Cancer Research* 1;65(3):1089-96 (2005).
Houghton and Abrignani, "Prospects for a vaccine against the hepatitis C virus," *Nature* 436(18):961-966 (2005).
Huang, Z., "Structural chemistry and therapeutic intervention of protein-protein interactions in immune response, human immunodeficiency virus entry, and apoptosis, " *Pharmacol. Ther.*, 86:201-215 (2000).
International Search Report for PCT Application No. PCT/US2006/022423, 11 pages (Jun. 18, 2007).
International Search report for PCT Application No. PCT/US2007/088851; 7 pages, (Sep. 24, 2008).
International Search Report from PCT Application No. PCT/US2009/066023, 6 pages (mailed on Aug. 2, 2010).
Ishida et al., "Induced expression of PD-1, a novel member of the immunoglobulin gene superfamily, upon programmed cell death," *EMBO J.*, 11(11):3887-3895 (1992).
Iwai et al., "Involvement of PD-L1 on tumor cells in the escape from host immune system and tumor immunotherapy by PD-L1 blockade," *Proc Natl. Acad. Sci. U S A.* 99(19):12293-7. (Epub 2002).
Iwai et al., "PD-1 inhibits antiviral immunity at the effector phase in the liver," *Journal of Experimental Medicine* 198(1): 39-50 (Jul. 7, 2003).

(56) References Cited

OTHER PUBLICATIONS

Kanai et al., "Blockade of B7-H1 Suppresses the Development of Chronic Intestinal Inflammation," *J. Immunol.*, 171:4156-4163 (2003).
Keir et al., "PD-1 Regulates Self-Reactive CD8 T Cell Responses to Antigen in Lymph Nodes and Tissues," *The Journal of Immunology*, 179:5064-5070 (2007).
Keir et al., "Tissue Expression of PD-L1 Mediates Peripheral T Cell Tolerance," *The Journal of Experimental Medicine*, 203(4):883-895 (2006).
Klenerman and Zinkernagel, "Clinical Investigation of Mice and Men: Cytotoxic T Cells and AIDS pathogenesis," The AIDS Reader 9(7): 474-480 (1999).
Klenerman and Zinkernagel, "What can we learn about human immunodeficiency virus infection from a study of lymphocytic choriomeningitis virus?" *Immunological Reviews* 159: 5-16 (1997).
Klenerman et al., "Of Mice and Men: Cytotoxic T Cells and AIDS Pathogenesis," *AIDS Reader*, 9(7):474-480 (1999).
Knutson et al., "Adoptive T-Cell Therapy for the Treatment of Solid Tumours," *Expert Opin. Biol. Ther.* 2(1):55-66 (2002).
Koga et al., "Blockade of the Interaction Between PD-1 and PD-L1 Accelerates Graft Arterial Disease in Cardiac Allografts," *Arterioscler. Thromb. Vasc. Biol.*, 24:2057-2062 (2004).
Kozlov and Chernykh, "Current Problems in Cancer Immunotherapy," Bulletin SB Rams 2(112): 13-19 (2004) (in Russian with English language translation).
Krummel et al., "CTLA-4 Engagement Inhibits IL-2 Accumulation and Cell Cycle Progression upon Activation of Resting T Cells," *J. Exp. Med.*, 183:2533-2540 (1996).
Lambert et al., "Safety and immunogenicity of HIV recombinant envelope vaccines in HIV-infected infants and children," *Journal of Acquired Immune Deficiency Syndromes & Human Retrovirology* 19(5):451-461 (1998).
Latchman et al., "PD-L2 is a second ligand for PD-1 and inhibits T cell activation," *Nat. Immunol.*, 2(3):261-268 (2001).
Le Blanc et al., "HLA expression and immunologic properties of differentiated and undifferentiated mesenchymal stem cells," *Exp. Hematol.*, 31:890-896 (2003).
Leiberman et al., "Safety of Autologous, EX Vivo-Expanded Human Immunodeficiency Virus (HIV)-Specific Cytotoxic T-Lymphocyte Infusion in HIV-Infected Patients," *Blood* 90:2196-2206 (1997).
Letvin, "Progress Toward an HIV vaccine," *Annu. Rev.* 56:213-233 (2005).
Liang et al., "The right place at the right time: novel B7 family members regulate effector T cell responses," *Curr. Opin. Immunol.*, 14:384-390 (2002).
Liu et al., "B7DC/PDL2 Promotes Tumor Immunity by a PD-1-independent Mechanism," *Journal of Experimental Medicine*, 197(12):1721-1730 (2003).
Liu et al., "CD8+T Cells Can Block Herpes Simplex Virus Type 1 (HSV-1) Reactivation from Latency in Sensory Neurons," *Journal of Experimental Medicine*, 191(9):1459-1466 (2000).
Loke and Allison, "PD-L1 and PD-L2 are differentially regulated by Th1 and Th2 cells," *PNAS* 100(9): 5336-5341 (Apr. 29, 2003).
Machuca et al., "Human Immunodeficiency Virus Type 2 Infection in Spain," *Intervirology*, 42:37-42 (1999).
Martins et al., "CTLA-4 Blockage Increases Resistance to Infection with the Intracellular Protozoan *Trypanosoma cruzi*," *Journal of Immunology* 172:4893-4901 (2004).
Metzler et al., "Solution structure of human CTLA-4 and delineation of a CD80/CD86 binding site conserved in CD28," *Nat. Struct. Biol.*, 4(7):527-531 (1997).
Moir et al., "Evidence for HIV-associated B cell exhaustion in a dysfunctional memory B cell compartment in HIV-infected viremic individuals," J. Exp. Med. 205(6): 1797-1805 (Jul. 14, 2008).
Morgan et al., "Cancer Regression in Patients After Transfer of Genetically Engineered Lymphocytes," Science 314:126-129 (2006).

Mueller et al., "PD-L1 has distinct functions in hematopoietic and nonhematopoietic cells in regulating T cell responses during chronic infection in mice," *Journal of Clinical Investigation* 120(7):2508-2515 (Jul. 2010).
Musey et al. "Cytotoxic-T-Cell Responses, Viral Load, and Disease Progression in Early Human Immunodeficiency Virus Type 1 Infection" *The New England Journal of Medicine*, 337(18):1267-1274 (1997).
Nishimura et al., "Autoimmune Dilated Cardiomyopathy in PD-1 Receptor-Deficient Mice," *Science*, 291:319-322 (2001).
Nishimura et al., "Development of Lupus-like Autoimmune Diseases by Disruption of the PD-1 Gene Encoding an ITIM Motif-Carrying Immunoreceptor," *Immunity*, 11:141-151 (1999).
Nishimura et al., "Developmentally regulated expression of the PD-1 protein on the surface of double-negative (CD4⁻ CD8⁻) thymocytes," *Int. Immunol.*, 8(5):773-780 (1996).
Nishimura et al., "Immunological studies on PD-1-deficient mice: implication of PD-1 as a negative regulator for B cell responses," *Inter. Immunol.*,10(10):1563-1572 (1998).
Ohigashi et al. "Clinical significance of programmed death-1 ligand-1 and programmed death-1 ligand-2 expression in human esophageal cancer," *Clin. Cancer Res.* 15;11(8):2947-53 (2005).
Ohshima et al., "The World Health Organization classification of malignant lymphoma: Incidence and clinical prognosis in HTLV-1-endemic area of Fukuoka," Pathology International 52:1-12 (Jan. 2002).
Ottensmeier, "The classification of lymphomas and leukemias," Chemico-Biological Interactions 135-136:653-664 (Jun. 1, 2001).
Ozkaynak et al., "Programmed Death-1 Targeting Can Promote Allograft Survival," *J. Immunol.*, 169:6546-6553 (2002).
Pascale et al., "Immunological Markers of Disease Progression in Patients Infected with the Human Immunodeficiency Virus," *Clinical and Diagnostic Laboratory Immunology* 4(4):474-477 (1997).
Petrovas et al., "PD-1 is a regulator of virus-specific CD8+T cell survival in HIV infection," *JEM*, 203(10):2281-2292, (Oct. 2, 2006).
Pilon-Thomas et al., "Blockade of Programmed Death Ligand 1 Enhances the Therapeutic Efficacy of Combination Immunotherapy Against Melanoma," *The Journal of Immunology*, 184:3442-3449 (2010).
Riddell and Greenberg, "Principles for adoptive T Cell therapy of human viral diseases," *Annual Review of Immunology*, 13:545-586, (1995).
Riley and June, "The road to recovery: translating PD-1 biology into clinical benefit," *Trends in Immunology*, 28(2):48-50, (Dec. 22, 2006).
Salama et al., "Critical Role of the Programmed Death-1 (PD-1) Pathway in Regulation of Experimental Autoimmune Encephalomyelitis," *J. Exp. Med.*, 198(1):71-78 (2003).
Saunders et al., "PD-L2:PD-1 involvement in T cell proliferation, cytokine production, and integrin-mediated adhesion," *Eur. J Immunol.*, 35:3561-3569 (2005).
Sedy et al., "B and T lymphocyte attenuator regulates T cell activation through interaction with herpesvirus entry mediator", *Nat. Immunol.*, 6(1)90-98 (2005).
Sharpe et al., "The B7-CD28 Superfamily," *Nat. Rev. Immunol.*, 1(2):116-126 (2002).
Shin et al., "Cooperative B7-1/2 (CD80/CD86) and B7-DC Costimulation of CD4+ T Cells Independent of the PD-1 Receptor," J. Exp. Med., 198(1):31-38 (2003).
Shinohara et al., "Structure and Chromosomal Localization of the Human PD-1 Gene (PDCD1)," *Genomics*, 23:704-706 (1994).
Song et al., "Enhancement of vaccine-induced primary and memory CD8(+) T-cell response by soluble PD-1," *J. Immunother.* 34: 297-306 (2011) (abstract).
Strome et al., "B7-H1 Blockade Augments Adoptive T-Cell Immunotherapy for Squamous Cell Carcinoma," *Cancer Research*, 63:6501-6505, (Oct. 1, 2003).
Subudhi et al., "Local expression of B7-H1 promotes organ-specific autoimmunity and transplant rejection," *J. Clin. Invest.*, 113(5):694-700 (2004).
SWISSPROT Acc No. Q9BQ51 "Butyrophilin precursor B7-DC (PD-1-lingand 2 protein)" (Feb. 9, 2008).

(56) References Cited

OTHER PUBLICATIONS

SWISSPROT Acc. No. Q9WUL5 "Butyrophilin-like protein" (Oct. 14, 2008).
Trabattoni et al., "B7-H1 is up-regulated in HIV infection and is a novel surrogate marker of disease progression," Blood, 1;101(7):2514-20 (2003).
Trautmann et al., "Upregulation of PD-1 expression on HIV-specific CD8+ T cells leads to reversible immune dysfunction," Nature Medicine, 12 (10):1198-1202 (2006).
Tseng et al., "B7-DC, a New Dendritic Cell Molecule with Potent Costimulatory Properties for T Cells," J. Exp. Med., 193(7):839-845 (2001).
Tsushima et al., Preferential contribution of B7-H1 to programmed death-1-mediated regulation of hapten-specific allergic inflammatory responses, Eur. J. Immunol., 33:2773-2782 (2003).
Velu et al., "Enhancing SIV-specific immunity in vivo by PD-1 blockade," Nature, 458(7235):206-210 (2009).
Walter et al., "Reconstruction of Cellular Immunity Against Cytomegalovirus in Recipients of Allogeneic Bone Marrow by Transfer of T-Cell Clones from the Donor," The New England Journal of Medicine 333:1038-1044 (1995).
Walunas et al., "CTLA-4 Ligation Blocks CD28-dependent T Cell Activation," J. Exp. Med., 183:2541-2550 (1996).
Wang et al., "Molecular Modeling and Functional Mapping of B7-H1 and B7-DC Uncouple Costimulatory Function from PD-1 Interaction," J. Exp. Med., 197(9):1083-1091 (2003).
Wang et al., "T Lymphocyte Co-Signaling Pathways of the B7-CD28 Family," Cellular & Molecular Immunology 1(1):37-42 (2004).
Webster et al., "Targeting Molecular and Cellular Inhibiting Mechanisms for Improvement of Antitumor Memory Response Reactivated by Tumor Cell Vaccine," Journal of Immunology 179(5):2860-2869 (2007).
Wherry et al., "Lineage Relationship and Protective Immunity of Memory CD8 T Cell Subsets," Nature Immunology 4: 225-34 (2003).
Yao and Chen, "Reviving Exhausted T Lymphocytes During Chronic Virus Infection by B7-H1 Blockade," TRENDS in Molecular Medicine, 12(6):244-246 (2006).
Yee et al., "Adoptive T cell therapy using antigen-specific CD8+ T cell clones for the treatment of patients with metastatic melanoma: In vivo persistence, migration, and antitumor effect of transferred T cells," PNAS, 99(25):16168-16173 (2002).
Yee et al., "Adoptive T-Cell Therapy of Cancer," Hematology/Oncology Clinics of North America, 20(3):711-733 (2006).
Yershov and Ospelnikova, "The Current Arsenal of Antiherpetic Medications," Infections and Antimicrobial Therapy, 3(4) (2001), in Russian with English language translation.
Ansell et al., "PD-1 blockade with nivolumab in relapsed or refractory Hodgkin's Lymphoma," New Engl. J. Med., pp. 1-9 (Dec. 6, 2014).
Dorfman et al., "Programmed death-1 (PD-1) is a marker of germinal center-associated T Cells and angioimmunoblastic T-Cell lymphoma," Am. J. Surg. Pathol. 30:802-810 (2006).
He et al., "Blocking programmed death-1 ligand-PD-1 interactions by local gene therapy results in enhancement of antitumor effect of secondary lymphoid tissue chemokine," J. Immunol. 173(8):4919-4928 (Aug. 16, 2004).
Poppema and van den Berg, "Interaction between host T cells and Reed-Sternberg cells in Hodgkin lymphomas," Cancer Biology 10:345-350 (2000).
Saudemont and Quesnel, "In a model of tumor dormancy, long-term persistent leukemic cells have increased B7-H1 and B7.1 expression and resist CTL-mediated lysis," Blood 104(7):2124-2133 (Oct. 1, 2004).
Akpek et al., "A clinician's guide to the updated REAL/WHO classification of non-Hodgkin's lymphoma: part I (indolent lymphomas)," Turkish Journal of Cancer 30(1): 5-14 (2000).
Annual Review of Immunity 171-177 (2004) (in Japanese).
Blank et al., "PD-L1/B7H-1 inhibits the effector phase of tumor rejection by T cell receptor (TCR) transgenic CD8+ T cells," Cancer Research 1140-1145 (Feb. 1, 2004).
English language translation of Notice of Reasons for Rejection from related Japanese Patent Application No. 2014-136588, 6 pages (mailed Mar. 28, 2016).
Hargreaves et al., "Selective depletion of activated T cells: the CD40L-specific antibody experience," Trends in Molecular Medicine 10(3):130-135 (Mar. 20004).
"Hodgkin's lymphoma" Merck Manual 18th edition [online], Internet URL: <http://merckmanual.jp/mmpej/print/sec11/ch143/ch143b.html> (w/copy of webpage in English).
Iwai et al., "PD-1 blockade inhibits hematogenous spread of poorly immunogenic tumor cells by enhanced recruitment of effector T cells," Int. Immunol. 17(2):133-144 (2004).
Levy et al., "Impaired lymphocyte function in untreated Hodgkin's disease," The New England Journal of Medicine 290:181-186 (Jan. 24, 1974).
Marshall et al., "Immunosuppressive regulatory T cells are abundant in the reactive lymphocytes of Hodgkin lymphoma," Blood 103(5): 1755-1762 (Mar. 1, 2004).
NCBI GenBank Acc No. AF329193 "Homo sapiens butyrophilin precursor B7-DC mRNA, complete cds" (Apr. 10, 2001).
NCBI GenBank Acc No. AF142780 "Mus musculus butyrophilin-like protein (Btdc) mRNA, complete cds," (Apr. 12, 2001).
NCBI GenBank Acc No. AF344424 "Homo sapiens PD-1-ligand 2 protein (PDL2) mRNA, complete cds," (Apr. 8, 2002).
NCBI GenBank Acc No. AK001872 "Homo sapiens cDNA FLJ11010 fis, clone PLACE1003145" (Jan. 9, 2008).
NCBI GenPept Acc No. Q9BQ51 "Butyrophilin precursor B7-DC (PD-1-lingand 2 protein)" (Feb. 9, 2008).
NCBI GenBank Acc No. AL162253 "Human DNA sequence from clone RP11-574F11 on chromosome 9 Contains the gene for B7-H1 protein (PD-L1), the gene for programmed death ligand 2 (PDL2) (PDCD1L2) and a novel gene, complete sequence" (Jan. 13, 2009).
NCBI GenPept Acc. No. AAH07485 "Golga4 protein" (Feb. 13, 2004).
NCBI GenPept Acc. No. AAH14818 "NADH dehydrogenase (ubiquinone) flavoprotein 1" (Dec. 2, 2006).
NCBI GenPept Acc. No. Q9WUL5 "Butyrophilin-like protein" (Oct. 14, 2008).
Records of the plenary session and academic meetings of Japanese Society for Immunology 34:228, Internet URL: < http://www.life-science-dictionary.com/weblsd/c/begin/academic meeting> (2004) (in Japanese).
Records of the plenary session and academic meetings of Japanese Society for Immunology 34:270, Internet URL: <http://www.life-science-dictionary.com/weblsd/c/begin/academic meeting> (2004) (in Japanese).
Rosenwald et al., "Molecular diagnosis of primary mediastinal B cell lymphoma identifies a clinically favorable subgroup of diffuse large B cell lymphoma related to Hodgkin lymphoma," Journal of Experimental Medicine 198(6):851-862 (Sep. 15, 2003).
Sotrel and Dal Canto, "HIV-1 and its causal relationship to immunosuppression and nervous system disease in AIDS: A review," Human Pathology 31: 1274-1298 (2000).

\* cited by examiner

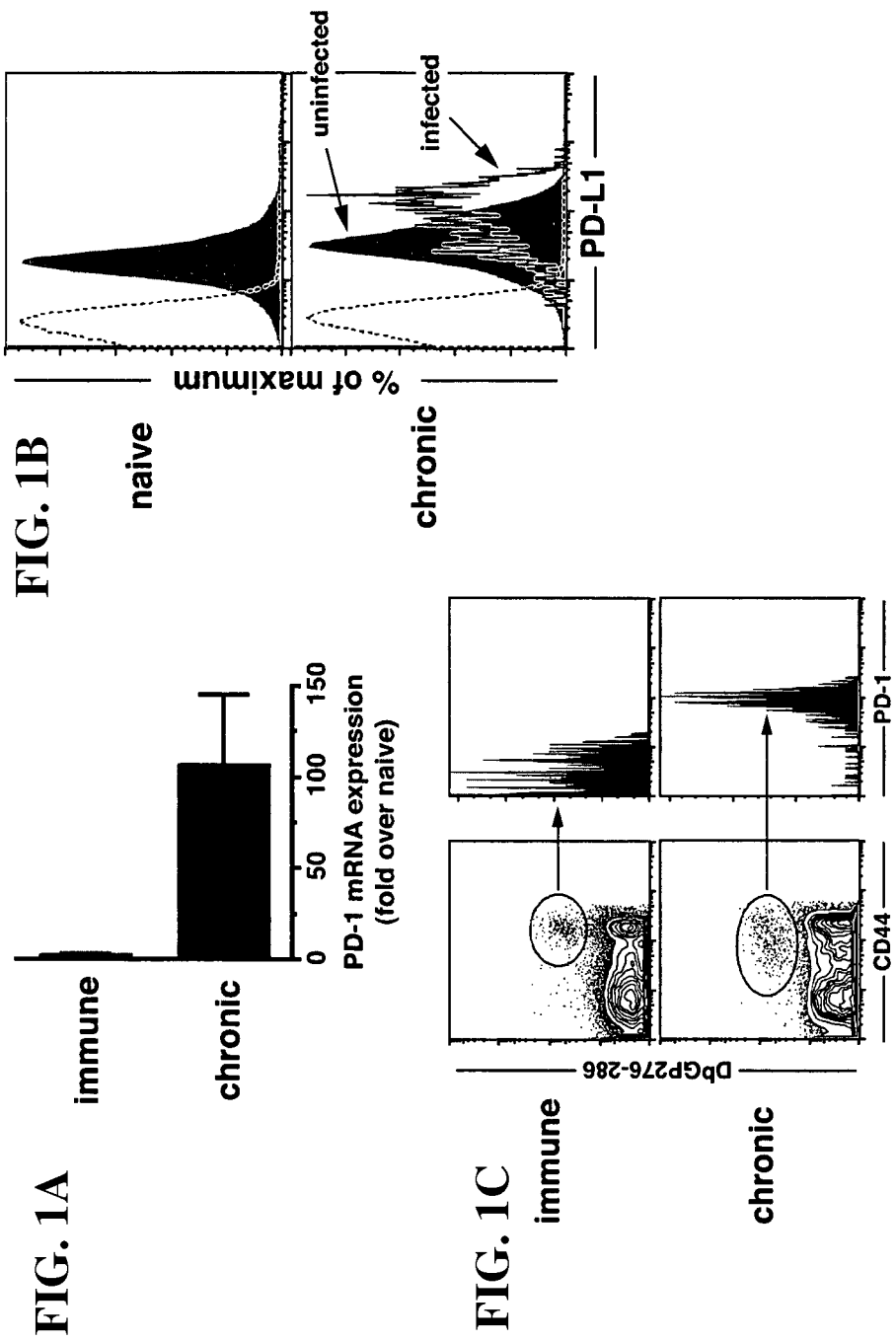

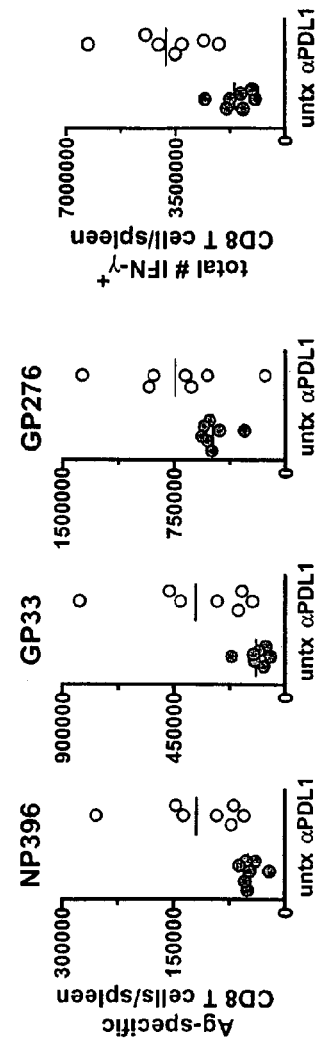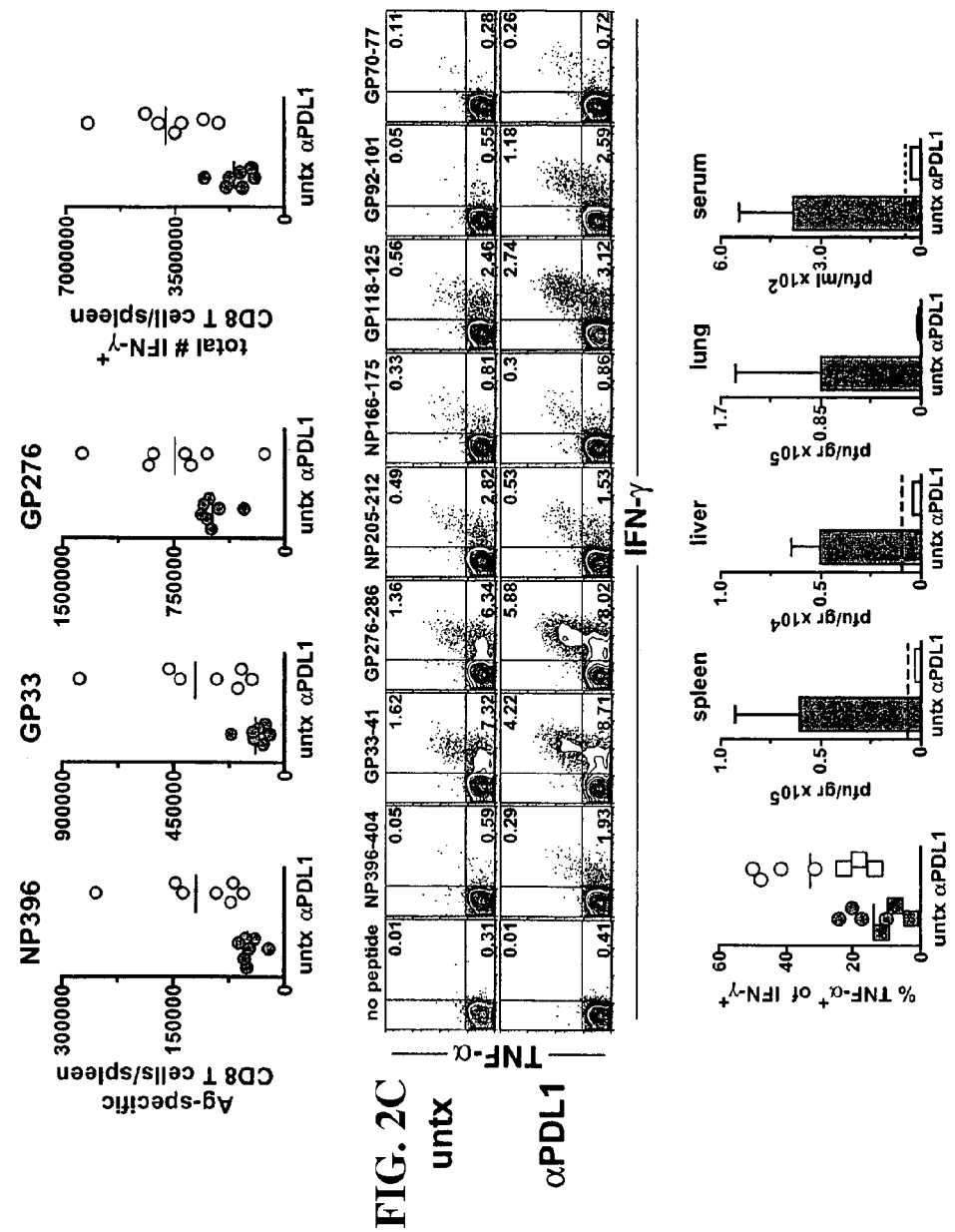
FIG. 2A FIG. 2B FIG. 2C FIG. 2D FIG. 2E

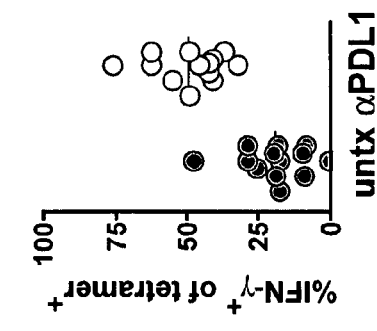
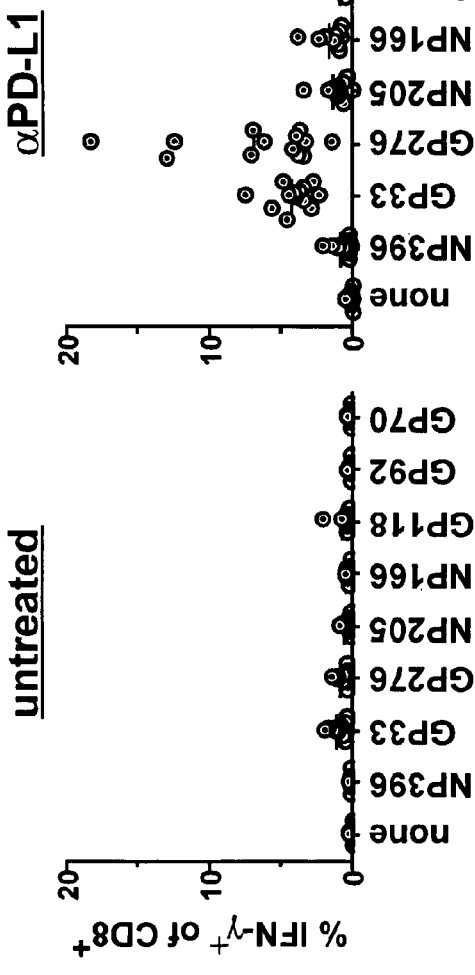
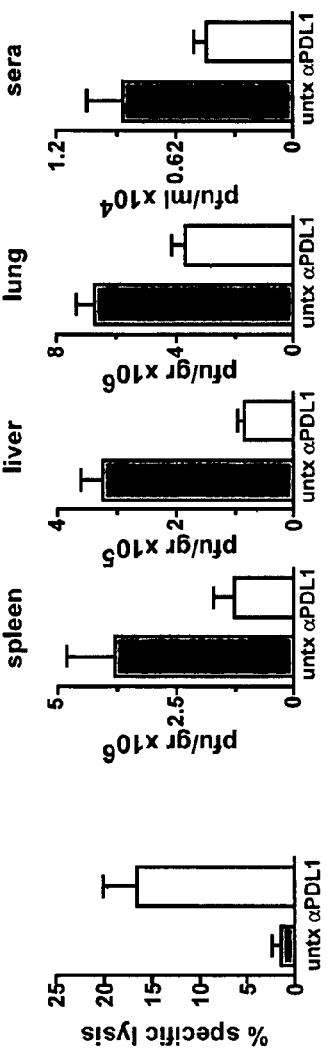
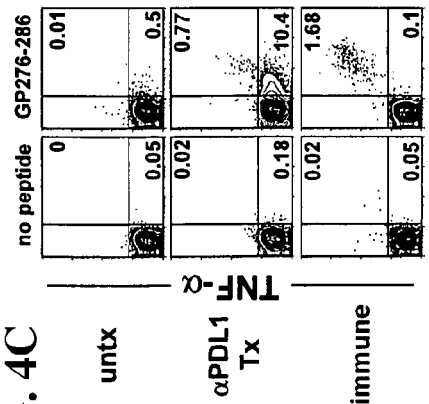
FIG. 4A
FIG. 4B
FIG. 4C
FIG. 4D
FIG. 4E

US 9,457,080 B2

METHODS AND COMPOSITIONS FOR THE TREATMENT OF PERSISTENT INFECTIONS AND CANCER BY INHIBITING THE PROGRAMMED CELL DEATH 1 (PD-1) PATHWAY

RELATED APPLICATIONS

This is a continuation of U.S. patent application Ser. No. 11/449,919, filed on Jun. 8, 2006, which in turn claims the benefit of U.S. provisional application 60/688,872, filed on Jun. 8, 2005. Both of the prior applications are incorporated herein by reference in their entirety.

STATEMENT AS TO FEDERALLY SPONSORED RESEARCH

This invention was made with government support under grant numbers AI39671 and CA84500 awarded by the National Institutes of Health. The government has certain rights in the invention.

FIELD OF THE INVENTION

In general, the present invention relates to methods and compositions for the treatment of persistent infections and cancer.

BACKGROUND OF THE INVENTION

Although the development of preventative vaccines has significantly reduced the mortality rate of viral infections, the use of such vaccines against viruses that cause persistent infections (e.g., hepatitis C virus) has been met with limited success. In contrast to viruses that cause acute and self-limited infections, the immune response that is mounted against persistent infection-causing microbes is often transient and insufficient to clear the infection. As a result, the infectious microbe remains within the infected subject for extended periods of time, without necessarily causing constant host damage.

A major impediment in the eradication of persistent infection-causing microbes is the ability of such microbes to evade the immune system of the host organism. For example, certain viruses and parasites down-regulate the expression of host molecules necessary for efficient T cell recognition of infected cells. Persistent infections also cause the functional impairment of antigen specific CD8+ T cells, which are vital to the control and eradication of viral infections. Although the combination of therapeutic vaccines with cytokine adjuvants has been encouraging, the resulting immune responses have not successfully eradicated the pathogen.

Thus, better methods are needed to treat, prevent, or alleviate persistent infections.

SUMMARY OF THE INVENTION

The present invention provides methods and compositions for the treatment, prevention, or reduction of, or alternatively the alleviation of one or more symptoms of, a persistent infection or cancer. The invention is based on the discovery that antigen specific CD8+ T cells become functionally tolerant ('exhausted') to the infectious agent following the induction of the Programmed Death-1 polypeptide (PD-1). Accordingly, by reducing the expression or activity of PD-1, PD-L1 or PDL2, the proliferation of functionally tolerant CD8+ T cells, the production of cytokines, and the rate of an infectious agent (e.g., viral, bacterial, fungal, parasite, mycoplasm or cancer) clearance is increased such that the immune response specific to the infectious agent is enhanced.

Accordingly, the invention provides a method of alleviating or preventing a symptom of a persistent infection (e.g., a viral infection, a bacterial infection, a fungal infection, a mycoplasm infection and a parasitic infection) or cancer by administering to a subject in need thereof (e.g., a human) a compound that reduces the activity or expression of a member of the CD28-like family (e.g., PD-1, CTLA-4, BTLA and a functional fragment or variant thereof) or CD28-like family ligands (e.g., PD-L1 or PD-L2). Alternatively, the subject is administered an antigen-specific T cell or B cell that has been contacted with an compound that reduces the expression or activity of a PD-1 polypeptide in the cell. For example, the antigen specific T cell or B cell is specific to a viral antigen. The T cell or B cell is derived from an autologous source or is derived from another subject of the same or different species as the subject being treated.

In addition, the invention features a method of increasing the cytotoxic activity of a T cell (e.g., anergic T cell or T cell having increased tolerance to antigens) by contacting the T cell with a compound that reduces the activity or expression of a PD-1 polypeptide.

In all foregoing aspects of the invention, persistent viral infections result from infections such as a hepatitis virus, a human immunodeficiency virus (HIV), a human T-lymphotrophic virus (HTLV), a herpes virus, an Epstein-Barr virus, or a human papilloma virus. Persistent viral infections may also include infections caused by a latent virus. Cancers include lymphoproliferative disorders such as angioimmunoblastic lymphoma and nodular lymphocyte Hodgkin lymphoma. Desirably, the compound of the invention increases an antigen specific immune response by increasing the cytotoxic T-cell activity (e.g., an increase in cytotoxic cytokine production such as IFNγ, TNFα, or IL-2, an increase in T cell proliferation, or an increase in viral clearance) in the subject being treated. For example, the compound reduces the expression or activity of a PD ligand 1 (PD-L1) or a PD ligand 2 (PD-L2) or reduces the interaction between PD-1 and PD-L1 or the interaction between PD-1 and PD-L2. Exemplary compounds include antibodies (e.g., an anti-PD-1 antibody, an anti-PD-L1 antibody, and an anti-PD-L2 antibody), RNAi molecules (e.g., anti-PD-1 RNAi molecules, anti-PD-L1 RNAi, and an anti-PD-L2 RNAi), antisense molecules (e.g., an anti-PD-1 antisense RNA, an anti-PD-L1 antisense RNA, and an anti-PD-L2 antisense RNA), dominant negative proteins (e.g., a dominant negative PD-1 protein, a dominant negative PD-L1 protein, and a dominant negative PD-L2 protein), and small molecule inhibitors. Antibodies include monoclonal antibodies, humanized antibodies, deimmunized antibodies, and Ig fusion proteins. An exemplary anti-PD-L1 antibody includes clone EH12.

In addition to the compound that reduces PD-1 expression or activity, the subject being treated may also be administered a vaccine that may or may not include an adjuvant or a prime booster shot. Optionally, the subject is administered a second compound, such as an antiviral compound (e.g., vidarabine, acyclovir, gancyclovir, valgancyclovir, nucleoside-analog reverse transcriptase inhibitor (NRTI) such as AZT (Zidovudine), ddI (Didanosine), ddC (Zalcitabine), d4T (Stavudine), or 3TC (Lamivudine), non-nucleoside reverse transcriptase inhibitor (NNRTI) such as nevirapine or delavirdine, protease inhibitor such as saquinavir, ritonavir, indinavir, or nelfinavir, ribavirin, and interferon), an antibacterial compound, an antifungal compound, an antiparasitic compound, an anti-inflammatory compound, antineoplastic compounds or an analgesic. The second compound may also be a compound that reduces the expression or activity of cytotoxic T lymphocyte antigen 4 (CTLA-4) or B and T lymphocyte attenuator (BTLA). Other exemplary compounds that may be administered to the subject are anti-CTLA-4 antibodies, anti-BTLA antibodies, anti-CD28 antibodies, anti-ICOS antibodies, anti-ICOS-L antibodies, anti-B7-1 antibodies, anti-B7-2 antibodies, anti-B7-H3 antibodies, and anti-B7-H4 antibodies.

The present invention further provides a method for identifying a candidate compound that modulates the activity or expression of a PD-1 polypeptide that includes the steps of: (a) contacting a cell expressing a PD-1 gene (e.g., PD-1 fusion gene) with a candidate compound; (b) measuring the expression or activity of PD-1 in the cell (e.g., by measuring the expression of PD-1 mRNA or protein); and (c) comparing the expression or activity of PD-1 in the cell compared to such expression or activity in a control cell not contacted with the compound. An increase or decrease in the expression or activity of PD-1 indicates the candidate compound as being useful for modulating the activity or expression of a PD-1 polypeptide.

Alternatively, the screening method may involve the steps of: (a) contacting a T cell that overexpresses a PD-1 gene with a candidate compound; and (b) determining the cytotoxic activity of the T cell; (c) comparing the cytotoxic activity of the T cell relative to such activity in a control cell not contacted with the compound. An increase or decrease in such activity identifies the candidate compound as being useful for modulating the activity or expression of a PD-1 polypeptide. Cytotoxic activity includes cytokine production, T cell proliferation, and viral clearance.

The invention further provides a screening method involving the steps of: (a) contacting a PD-1 polypeptide with a candidate compound; (b) determining whether the candidate compound interacts with the PD-1 polypeptide; and (c) identifying a candidate compound as useful for modulating PD-1 expression or activity. Desirably, the identified candidate compound interacts with the PD-1 polypeptide and reduces its activity.

The candidate compound identified by the screening methods described herein may reduce the interaction between PD-1 and PD-L1 or the interaction between PD-1 and PD-L2. The cell employed in any of the screening methods described herein include mammalian cells such as rodent cells or human cell. The cell is an immune cell, such as a T cell. Desirably, the PD-1 polypeptide used in such screening methods is a human PD-1 polypeptide.

Also provided herein is a method of diagnosing a subject as having or at risk of having a persistent infection or cancer involving the steps of: (a) providing a sample containing immune cells (e.g., T cell or B cell) from a subject, and (b) measuring the expression or activity of PD-1 in the sample. An increase in the expression or activity of PD-1 compared to such expression or activity in a control sample identifies the subject as having or at risk of having a persistent infection or cancer. Desirably, step (b) involves identifying antigen-specific immune cells, such as a viral antigen, bacterial antigen, parasitic antigen, or fungal antigen.

A method of selecting a treatment for a subject having or at risk of having a persistent infection or cancer is also described. This method involves the steps of: (a) providing a sample containing immune cells (e.g., T cell or B cell) from a subject; and (b) measuring the expression or activity of PD-1 in the immune cells, such that an increase in expression or activity of PD-1 compared to such expression or activity in a control sample identifies the subject as having or at risk of having a persistent infection or cancer; and (c) selecting a treatment for the subject diagnosed as having or at risk a persistent infection or cancer, such that the treatment includes a compound that reduces the expression or activity of PD-1. Desirably, step (b) involves identifying antigen-specific immune cells, such as a viral antigen, bacterial antigen, parasitic antigen, or fungal antigen.

Samples derived from subjects include blood samples, tissue biopsies, and bone marrow samples. Furthermore, control cells may be derived from a subject that does not have or at risk of having a persistent infection.

The invention further provides a composition that contains: (a) a compound that reduces the level or activity of PD-1; and (b) a second compound, such as an antiviral compound, an antibacterial compound, an antifungal compound, an antiparasitic compound, an anti-inflammatory compound, an analgesic, an anti-CTLA-4 antibody, an anti-BTLA antibody, an anti-CD28 antibody, an anti-ICOS antibody, an anti-ICOS-L antibody, an anti-B7-1 antibody, an anti-B7-2 antibody, an anti-B7-H3 antibody, or an anti-B7-H4 antibody.

The invention also provides a kit that contains (a) a compound that reduces the level or activity of PD-1; and (b) instructions for delivery of the compound to a subject. Alternatively, the kit contains (a) a first compound that reduces the level or activity of PD-1; (b) a second compound such as an antiviral compound, an antibacterial compound, an antifungal compound, an antiparasitic compound, an anti-inflammatory compound, an analgesic, an anti-CTLA-4 antibody, an anti-BTLA antibody, an anti-CD28 antibody, an anti-ICOS antibody, an anti-ICOS-L antibody, an anti-B7-1 antibody, an anti-B7-2 antibody, an anti-B7-H3 antibody, or an anti-B7-H4 antibody; and (c) instructions for delivery of the first compound and the second compound to a subject.

The present invention provides significant advantages over standard therapies for treatment, prevention, and reduction, or alternatively, the alleviation of one or more symptoms of persistent infections. Administration of the therapeutic agent that reduces the level or activity of PD-1 increases CD8+ T cell cytotoxicity, in turn increasing the immune response to the infectious agent having the ability to establish a persistent infection. In addition, the candidate compound screening methods provided by this invention allow for the identification of novel therapeutics that modify the injury process, rather than merely mitigating the symptoms.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A is a bar graph showing the levels of PD-1 mRNA in $D^b$GP33-41 and/or $D^b$GP276-286 specific T cells from naïve transgenic mice, lymphocytic choriomeningitis virus (LCMV) Armstrong immune (approximately 30 days post-infection) infected mice, or CD4-depleted LCMV-Cl-13 infected mice (approximately 30 days post-infection), as measured by gene array analysis.

FIG. 1B is a series of images of a flow cytometry experiment showing PD-1 surface expression on CD8+ tetramer+ T cells in LCMV Armstrong immune and CD4 depleted LCMV-Cl-13 infected mice approximately 60 days post-infection. Anergic CD8+ T cells express high levels of PD-1 polypeptide on the cell surface approximately 60 days after chronic infection with LCMV-Cl-13 virus (labeled "chronic"), but virus-specific CD8+ T cells do not express PD-1 polypeptide after clearance of an acute LCMV Armstrong infection (labeled "immune").

FIG. 1C is a series of images of a flow cytometry experiment demonstrating the presence of PD-L1 on splenocytes from chronically infected and uninfected mice. It demonstrates that PD-L1 expression is the highest on the splenocytes that are infected by the virus.

FIG. 2A is a series of scatter plots showing that when Cl-13 infected mice are treated from day 23 to 37 post-infection there was approximately a 3 fold increase in the number of DbNP396-404 specific and DbGP33-41 specific CD8 T cells compared to the untreated controls. In order to determine any changes in function IFN-γ and TNF-α production was measured in response to 8 different LCMV epitopes.

FIG. 2B is a scatter plot showing that when all the known CD8 T cell specificities are measured there is a 2.3 fold increase in total number of LCMV specific CD8 T cells.

FIG. 2C is a series of flow cytometry graphs showing IFN-γ and TNF-α production in response to eight different LCMV epitopes.

FIG. 2D is a scatter plot showing that more virus specific CD8 T cells in treated mice have the ability to produce TNF-α.

FIG. 2E is a series of bar charts showing that PD-L1 blockade also resulted in increased viral control in the spleen liver lung and serum.

FIG. 4A is a series of charts demonstrating the increase in IFN-γ producing DbGP276-286 and DbGP33-41 specific CD8+ T cells in anti-PD-L1-treated mice, as compared to controls. Higher frequencies of DbNP396-404, KbNP205-212, DbNP166-175, and DbGP92-101 specific CD8+ T cells were also detected in anti-PD-L1-treated mice.

FIG. 4B is a chart demonstrating that in anti-PD-L1-treated mice, 50% of DbGP276-286 specific CD8+ T cells produce IFN-γ, as compared to 20% of DbGP276-286 specific CD8+ T cells in control mice.

FIG. 4C is a series of images demonstrating that anti-PD-L1-treated chronically infected mice produce higher levels of TNF-α than untreated chronically infected mice, but still produce lower levels of TNF-α than immune mice infected with LCMV Armstrong virus.

FIG. 4D is a chart demonstrating that treatment of LCMV-Cl-13 infected mice with anti-PD-L1 renews ex vivo lytic activity of the virus-specific T cells, as compared to untreated infected mice, measured using a $^{51}$Cr release assay.

FIG. 4E is a series of charts demonstrating the reduction of viral titers in various organs following treatment of LCMV-Cl-13 infected mice with α-PD-L1. Viral titers decreased approximately 3 fold in the spleen, 4 fold in the liver, 2 fold in the lung, and 2 fold in serum after 2 weeks of anti-PD-L1 treatment, as compared to untreated mice.

DETAILED DESCRIPTION

Figure 3A:
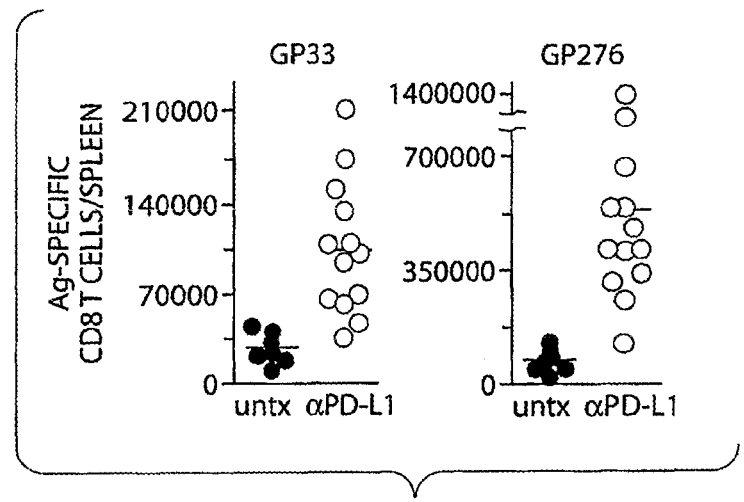
FIG. 3A is a graph demonstrating the increase in DbGP33-41 and DbGP276-286 specific CD8+ T cells (labeled "GP33" and "GP276") in CD4-depleted Cl-13 infected mice treated with anti-PD-L1 (labeled "αPD-L1") from day 46 to day 60 post-infection versus control (labeled "untx"), which demonstrates that mice treated with anti-PD-L1 contained approximately 7 fold more DbGP276-286 specific splenic CD8+ T cells and approximately 4 fold more DbGP33-41 specific splenic CD8+ T cells than untreated mice.

The use of antibiotics and vaccines in recent decades has significantly reduced the mortality rate due to microbial infections. The success of antimicrobial treatment modalities, however, has been limited by the ability of certain infectious agents to evade the immune system of the host organism and in turn, establish a persistent infection. For example, the immune response that is mounted against viruses such as hepatitis and HIV is not sufficient to clear the infectious agent, which remains in the infected subject. In such infections, antigen specific CD8+ T cells become functionally tolerant to the infectious agent, in a state known as 'anergy' or 'exhaustion'. Anergic T cells lose their cytotoxic activity, i.e., their ability to produce cytokines, proliferate, and clear the infectious agent.

The present invention is based upon the surprising discovery that T cell anergy is concomitant with an induction in PD-1 expression and that PD-1 expression correlates with certain types of lymphoproliferative disorders. Accordingly, the invention provides methods of increasing T-cell cytoxicity by contacting a T-cell with an agent that reduces the expression or activity of PD-1, PD-1 ligand (PD-L1) or PD-1 ligand 2 (PD-L2). More specifically, the invention provides methods of treating or preventing a persistent infection or lymphoproliferative disorders (e.g., cancers such as angioimmunoblastic lymphoma and nodular lymphocyte predominant Hodgkin lymphoma by administering to a subject an agent that reduces the expression or activity of PD-1. Reduction of PD-1, PD-L1 or PD-L2 expression or activity results in an increase in cytotoxic T cell activity, increasing the specific immune response to the infectious agent. The results provided herein show that the administration of anti-programmed death ligand-1 (PD-L1) blocking antibodies to persistently infected mice increased the cytotoxic activity of anergic T cells. Specifically, disruption of PD-1 signaling induced the expansion of anergic CD8+ T cells, enhanced cytokine production, and increased viral clearance. Furthermore, CD8+ T cells generated during persistent infections of CD4 depleted mice proliferated and regained much of their function upon anti-PD-L1 treatment.

In order for T cells to respond to foreign proteins, two signals must be provided by antigen-presenting cells (APCs) to resting T lymphocytes. The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional. Costimulation is neither antigen-specific, nor MHC-restricted and is provided by one or more distinct cell surface polypeptides expressed by APCs. If T cells are only stimulated through the T cell receptor, without receiving an additional costimulatory signal, they become nonresponsive, anergic, or die, resulting in downmodulation of the immune response.

The CD80 (B7-1) and CD86 (B7-2) proteins, expressed on APCs, are critical costimulatory polypeptides. While B7-2 plays a predominant role during primary immune responses, B7-1 is upregulated later in the course of an immune response to prolong primary T cell responses or costimulating secondary T cell responses. B7 polypeptides are capable of providing costimulatory or inhibitory signals to immune cells to promote or inhibit immune cell responses. For example, when bound to a costimulatory receptor, PD-L1 (B7-4) induces costimulation of immune cells or inhibits immune cell costimulation when present in a soluble form. When bound to an inhibitory receptor, B7-4 molecules can transmit an inhibitory signal to an immune cell. Exemplary B7 family members include B7-1, B7-2, B7-3 (recognized by the antibody BB-1), B7h (PD-L1), and B7-4 and soluble fragments or derivatives thereof. B7 family members bind to one or more receptors on an immune cell, such as CTLA4, CD28, ICOS, PD-1 and/or other receptors, and, depending on the receptor, have the ability to transmit an inhibitory signal or a costimulatory signal to an immune cell.

CD28 is a receptor that is constitutively expressed on resting T cells. After signaling through the T cell receptor, ligation of CD28 and transduction of a costimulatory signal induces T cells to proliferate and secrete IL-2. CTLA4 (CD 152), a receptor homologous to CD28, is absent on resting T cells but its expression is induced following T cell activation. CTLA4 plays a role in negative regulation of T cell responses. ICOS, a polypeptide related to CD28 and CTLA4, is involved in IL-10 production. PD-1, the receptor to which PD-L1 and PD-L2 bind, is also rapidly induced on the surface of T-cells. PD-1 is also expressed on the surface of B-cells (in response to anti-IgM) and on a subset of thymocytes and myeloid cells.

Engagement of PD-1 (for example by crosslinking or by aggregation), leads to the transmission of an inhibitory signal in an immune cell, resulting in a reduction of immune responses concomitant with an increase in immune cell anergy. PD-1 family members bind to one or more receptors, such as PD-L1 and PD-L2 on antigen presenting cells.

PD-L1 and PD-L2, both of which are human PD-1 ligand polypeptides, are members of the B7 family of polypeptides. Each PD-1 ligand contains a signal sequence, an IgV domain, an IgC domain, a transmembrane domain, and a short cytoplasmic tail. These ligands are expressed in placenta, spleen, lymph nodes, thymus, and heart. PD-L2 is also expressed in the pancreas, lung, and liver, while PD-L1 is expressed in fetal liver, activated T-cells and endothelial cells. Both PD-1 ligands are upregulated on activated monocytes and dendritic cells.

Definitions

As used herein, by "persistent infection" is meant an infection in which the infectious agent (e.g., virus, bacterium, parasite, mycoplasm, or fungus) is not cleared or eliminated from the infected host, even after the induction of an immune response. Persistent infections may be chronic infections, latent infections, or slow infections. While acute infections are relatively brief (lasting a few days to a few weeks) and resolved from the body by the immune system, persistent infections may last for months, years, or even a lifetime. These infections may also recur frequently over a long period of time, involving stages of silent and productive infection without cell killing or even producing excessive damage to the host cells. The causative infectious agents may also be detected in the host (e.g., inside specific cells of infected individuals) even after the immune response has resolved, using standard techniques. Mammals are diagnosed as having a persistent infection according to any standard method known in the art and described, for example, in U.S. Pat. Nos. 6,368,832, 6,579,854, and 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference. For example, a subject may be diagnosed as having a persistent Chlamydial infection following the detection of Chlamydial species in a biological sample from this individual using PCR analysis. Mammals need not have not been diagnosed with a persistent infection to be treated according to this invention. Microbial agents capable of establishing a persistent infection include viruses (e.g., papilloma virus, hepatitis virus, human immune deficiency virus, and herpes virus), bacteria (e.g., *Eschericchia coli* and *Chlamydia* spp.), parasites, (e.g., *Plasmodium, Leishmania* spp., *Schistosoma* spp., *Trypanosoma* spp., *Toxoplasma* spp.) and fungi.

By "alleviating a symptom of a persistent infection" is meant ameliorating any of the conditions or symptoms associated with the persistent infection before or after it has occurred. Alternatively, alleviating a symptom of a persistent infection may involve reducing the infectious microbial (e.g., viral, bacterial, fungal, mycoplasm, or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. Desirably, the persistent infection is completely cleared as detected by any standard method known in the art, in which case the persistent infection is considered to have been treated. A patient who is being treated for a persistent infection is one who a medical practitioner has diagnosed as having such a condition. Diagnosis may be by any suitable means. Diagnosis and monitoring may involve, for example, detecting the level of microbial load in a biological sample (e.g., tissue biopsy, blood test, or urine test), detecting the level of a surrogate marker of the microbial infection in a biological sample, detecting symptoms associated with persistent infections, or detecting immune cells involved in the immune response typical of persistent infections (e.g., detection of antigen specific T cells that are anergic) A patient in whom the development of a persistent infection is being prevented may or may not have received such a diagnosis. One in the art will understand that these patients may have been subjected to the same standard tests as described above or may have been identified, without examination, as one at high risk due to the presence of one or more risk factors (e.g., family history or exposure to infectious agent).

As used herein, by "PD-1" is meant a polypeptide that forms a complex with PD-L1 or PD-L2 proteins and is therefore involved in immune responses, such as the co-stimulation of T cells. The PD-1 proteins of the invention are substantially identical to the naturally occurring PD-1 (see, for example, Ishida et al. EMBO J. 11:3887-3895, 1992, Shinohara et al. Genomics 23:704-706, 1994; and U.S. Pat. No. 5,698,520, incorporated by reference herein). PD-1 signaling may reduce, for example, CD8+ T cell cytoxicity by reducing T cell proliferation, cytokine production, or viral clearance. According to this invention, the PD-1 polypeptide reduces CD8+ T cell cytotoxic activity by at least 5%, 10%, 20%, 30%, 40%, 50%, 60%, 70%, 80%, 90%, or more than 100% below control levels as measured by any standard method.

By a "PD-1 gene" is meant a nucleic acid that encodes a PD-1 protein.

By "PD-1 fusion gene" is meant a PD-1 promoter and/or all or part of a PD-1 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and .beta.-galactosidase.

By "reduce the expression or activity of PD-1" is meant to reduce the level or biological activity of PD-1 relative to the level or biological activity of PD-1 in an untreated control. According to this invention, such level or activity is reduced by at least 10%, 20%, 30%, 40%, 50%, 60%, 70%, 80%, 90%, 100%, or even greater than 100%, relative to an untreated control. For example, the biological activity of PD-1 is reduced if binding of PD-1 to PD-L1, PD-L2, or both is reduced, thereby resulting in a reduction in PD-1 signaling and therefore resulting in an increase in CD8+ T cell cytotoxicity. As used herein, the term "activity" with respect to a PD-1 polypeptide includes any activity which is inherent to the naturally occurring PD-1 protein, such as the ability to modulate an inhibitory signal in an activated immune cell, e.g., by engaging a natural ligand on an antigen presenting cell. Such modulation of an inhibitory signal in an immune cell results in modulation of proliferation of and/or cytokine secretion by an immune cell. PD-1 may also modulate a costimulatory signal by competing with a costimulatory receptor for binding of a B7 molecule. Thus, the term "PD-1 activity" includes the ability of a PD-1 polypeptide to bind its natural ligand(s), the ability to modulate immune cell costimulatory or inhibitory signals, and the ability to modulate the immune response. Accordingly, reducing PD-1 activity includes reducing the interaction of PD-1 to PD-L1 or PD-L2. This can be accomplished for example by blocking PD-L1 or PD-L2.

By "immune cell" is meant a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

By "T cell" is meant a CD4+ T cell or a CD8+ T cell. The term T cell includes both TH1 cells and TH2 cells.

The term "T cell cytoxicity" includes any immune response that is mediated by CD8+ T cell activation. Exemplary immune responses include cytokine production, CD8+ T cell proliferation, granzyme or perforin production, and clearance of the infectious agent.

By "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, re-exposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. Science 257:1134, 1992). Anergic antigen specific T cells may have a reduction of at least 10%, 20%, 30%, 40%, 50%, 60%, 70%, 80%, 90%, 95%, or even 100% in cytotoxic activity relative a corresponding control antigen specific T cell.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a PD-1, PD-L1, or PD-L2 specific antibody. A purified antibody may be obtained, for example, by affinity chromatography using recombinantly-produced protein or conserved motif peptides and standard techniques.

By "specifically binds" is meant an antibody that recognizes and binds an antigen such as a PD-1, PD-L1, or PD-L2 polypeptide but that does not substantially recognize and bind other non-antigen molecules in a sample, e.g., a biological sample, that naturally includes protein. A preferred antibody binds to the PD-1, PD-L1, or PD-L2 polypeptides disclosed in U.S. Pat. No. 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference.

By "neutralizing antibodies" is meant antibodies that interfere with any of the biological activities of a PD-1 polypeptide, particularly the ability of a PD-1 polypeptide to reduce an immune response such as the cytotoxicity of T cells. The neutralizing antibody may reduce the ability of a PD-1 polypeptide to reduce an immune response by, preferably 50%, more preferably by 70%, and most preferably by 90% or more. Any standard assay to measure immune responses, including those described herein, may be used to assess potentially neutralizing antibodies.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical" nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. See, e.g., F. Ausubel et al., Current Protocols in Molecular Biology, John Wiley & Sons, New York, N.Y., 1998, hereby incorporated by reference.

By "substantially pure" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "isolated DNA" is meant DNA that is free of the genes which, in the naturally occurring genome of the organism from which the given DNA is derived, flank the DNA. Thus, the term "isolated DNA" encompasses, for example, cDNA, cloned genomic DNA, and synthetic DNA.

By "an effective amount" is meant an amount of a compound, alone or in a combination, required to reduce or prevent hypertension or to treat or prevent a chronic infection in a mammal. The effective amount of active compound(s) varies depending upon the route of administration, age, body weight, and general health of the subject. Ultimately, the attending physician or veterinarian will decide the appropriate amount and dosage regimen.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof. For example, a useful candidate compound according to the present invention reduces binding of PD-1 to PD-L1, PD-L2, or both.

The term "pharmaceutical composition" is meant any composition, which contains at least one therapeutically or biologically active agent and is suitable for administration to the patient. Any of these formulations can be prepared by well-known and accepted methods of the art. See, for example, *Remington: The Science and Practice of Pharmacy*, 20.sup.th edition, (ed. A R Gennaro), Mack Publishing Co., Easton, Pa., 2000.

Methods of Treating

T-cell cytotoxicity is increased by contacting a T-cell with a compound that reduces the expression or activity of PD-1. The T-cell is a naive T-cell, memory T-cell or activated T-cell. Alternatively, the T-cell is an antigen specific T-cell. The antigen specific T cells is anergic or tolerant to the infectious agent. T-cell cytotoxicity is characterized by an increase in cell proliferation and cytokine release.

The methods are useful to alleviate the symptoms of a variety of infections and cancers. An infection or cancer is treated, prevented or a symptom is alleviated by administering to a subject a PD-1 inhibitor. The subject is a mammal such as human, a primate, mouse, rat, dog, cat, cow, horse, and pig. The subject is suffering from or at risk of developing infection. A subject suffering from or at risk of developing infection is by standard methods suitable for the particular infection.

The infection, e.g., bacterial, viral, fungal, mycoplasm, or parasitic is a persistent infection. Persistent infections, in contrast to acute infections are not effectively cleared by the induction of a host immune response. The infectious agent and the immune response reach equilibrium such that the infected subject remains infectious over a long period of time without necessarily expressing symptoms. Persistent infections include for example, latent, chronic and slow infections.

In a chronic infection, the infectious agent can be detected in the body at all times. However, the signs and symptoms of the disease may be present or absent for an extended period of time. Examples of chronic infection include hepatitis B (caused by HBV) and hepatitis C (caused by HCV) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, measles virus, rubella virus, human immunodeficiency virus (HIV), human T cell leukemia virus I, and human T cell leukemia virus II. Parasitic persistent infections may arise as a result of infection by *Leishmania, Toxoplasma, Trypanosoma, Plasmodium, Schistosoma,* and *Encephalitozoon*.

In a latent infection, the infectious agent (e.g., virus) is seemingly inactive and dormant such that the subject does always exhibit signs or symptoms. In a latent viral infection, the virus remains in equilibrium with the host for long periods of time before symptoms again appear; however, the actual viruses cannot be detected until reactivation of the disease occurs. Examples of latent infections include infections caused by HSV-1 (fever blisters), HSV-2 (genital herpes), and VZV (chickenpox-shingles).

In a slow infection, the infectious agents gradually increase in number over a very long period of time during which no significant signs or symptoms are observed. Examples of slow infections include AIDS (caused by HIV-1 and HIV-2), lentiviruses that cause tumors in animals, and prions.

In addition, persistent infections often arise as late complications of acute infections. For example, subacute sclerosing panencephalitis (SSPE) can occur following an acute measles infection or regressive encephalitis can occur as a result of a rubella infection.

Cancers include for example angioimmunoblastic lymphoma or nodular lymphocyte predominant Hodgkin lymphoma.

Angioimmunoblastic lymphoma (AIL) is an aggressive (rapidly progressing) type of T-cell non-Hodgkin lymphoma marked by enlarged lymph nodes and hypergammaglobulinemia (increased antibodies in the blood). Other symptoms may include a skin rash, fever, weight loss, positive Coomb's test or night sweats. This malignancy usually occurs in adults. Patients are usually aged 40-90 years (median around 65) and are more often male. As AIL progresses, hepatosplenomegaly, hemolytic anemia, and polyclonal hypergammaglobulinemia may develop. The skin is involved in approximately 40-50% of patients.

Nodular lymphocyte predominant Hodgkin lymphoma is a B cell neoplasm that appears to be derived from germinal center B cells with mutated, non-functional immunoglobulin genes. Similar to angioimmunoblastic lymphoma, neoplastic cells are associated with a meshwork of follicular dendritic cells. PD-1 expression is seen in T cells closely associated with neoplastic CD20+ cell in nodular lymphocyte predominant Hodgkin lymphoma, in a pattern similar to that seen for CD57+ T cells. CD57 has been identified as another marker of germinal center-associated T cells, along with CXCR5, findings which support the conclusion that the neoplastic cells in nodular lymphocyte predominant Hodgkin lymphoma have a close association with germinal center-associated T cells.

An inhibitor of PD-1 is any agent having the ability to reduce the expression or the activity of PD-1, PD-L1 or PD-2 in a cell. PD-1 expression or activity is reduced by at least 10%, 20%, 30%, 40%, 50%, 60%, 70%, 80%, 90%, or 100% compared to such expression or activity in a control cell. The control cell is a cell that has not been treated with the PD-1 inhibitor. PD-1 expression or activity is determined by any standard method in the art, including those described herein. Optionally, the PD-1 inhibitor inhibits or reduces binding of PD-1 to PD-L1, PD-L2, or both. PD-1 inhibitors include polypeptides, polynucleotides, small molecule antagonists, or siRNA.

A PD-1 inhibitor polypeptide includes, for example, an antibody or fragment thereof that reduces PD-1 expression or signaling. Exemplary antibodies include anti-PD-1 antibodies, anti-PD-L1 antibodies, anti-PD-L2 antibodies, anti-CTLA-4 antibodies, anti-BTLA antibodies, anti-CD28 antibodies, anti-ICOS antibodies, anti-ICOS-L antibodies, an anti-B7-1 antibody, an anti-B7-2 antibody, anti-B7-H3 antibodies, or anti-B7-H4 antibodies.

Alternatively, the PD-1 inhibitor is a dominant negative protein or a nucleic acid encoding a dominant negative protein that interferes with the biological activity of PD-1 (i.e. binding of PD-1 to PD-L1, PD-L2, or both). A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative PD-1 has mutation such that it no longer able to binds PD-L1.

The dominant negative protein may be administered as an expression vector. The expression vector may be a non-viral vector or a viral vector (e.g., retrovirus, recombinant adeno-associated virus, or a recombinant adenoviral vector). Alternatively, the dominant negative protein may be directly administered as a recombinant protein systemically or to the infected area using, for example, microinjection techniques.

Small molecules includes, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The PD-1 inhibitor is an antisense molecule, an RNA interference (siRNA) molecule, or a small molecule antagonist that targets PD-1 expression or activity. By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense PD-1, PD-L1 or PD-L2 nucleic acid sequence, an anti-sense PD-1, PD-L1 or PD-L2 nucleic acid sequence or both. Optionally, the siRNA is constructed such that a single transcript has both the sense and complementary antisense sequences from the target gene, e.g., a hairpin. Binding of the siRNA to an PD-1, PD-L1 or PD-L2 transcript in the target cell results in a reduction in PD-1, PD-L1 or PD-L2 production by the cell. The length of the oligonucleotide is at least 10 nucleotides and may be as long as the naturally-occurring PD-1, PD-L1 or PD-L2 transcript. Preferably, the oligonucleotide is 19-25 nucleotides in length. Most preferably, the oligonucleotide is less than 75, 50, 25 nucleotides in length.

Other suitable PD-1 inhibitors are described in, for example, in U.S. Pat. No. 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference.

The preferred dose of the PD-1 inhibitor is a biologically active dose. A biologically active dose is a dose that will induce an increase in CD8+ T cell cytotoxic activity the increase in the immune response specific to the infectious agent. Desirably, the PD-1 inhibitor has the ability to reduce the expression or activity of PD-1 in antigen specific immune cells (e.g., T cells such as CD8+ T cells) by at least 5%, 10%, 20%, 30%, 40%, 50%, 60%, 70%, 80%, 90%, or more than 100% below untreated control levels. The levels or activity of PD-1 in immune cells is measured by any method known in the art, including, for example, Western blot analysis, immunohistochemistry, ELISA, and Northern Blot analysis. Alternatively, the biological activity of PD-1 is measured by assessing binding of PD-1 to PD-L1, PD-L2, or both. The biological activity of PD-1 is determined according to its ability to increase CD8+ T cell cytotoxicity including, for example, cytokine production, clearance of the infectious agent, and proliferation of antigen specific CD8+ T cells. Preferably, the agent that reduces the expression or activity of PD-1 can increase the immune response specific to the infectious agent by at least 5%, 10%, 20%, 30%, 40%, 50%, 60%, 70%, 80%, 90%, or more than 100% above untreated control levels. The agent of the present invention is therefore any agent having any one or more of these activities. Although the agent of the invention is preferably expressed in CD8+ T cells, it is understood that any cell that can influence the immune response to persistent infections is also amenable to the methods of the invention and include, for example, B cells.

Optionally, the subject is administered one or more additional therapeutic agents. Additional therapeutic agents include, for example, antiviral compounds (e.g., vidarabine, acyclovir, gancyclovir, valgancyclovir, nucleoside-analog reverse transcriptase inhibitor (NRTI) (e.g., AZT (Zidovudine), ddI (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon), antibacterial compounds, antifungal compounds, antiparasitic compounds, anti-inflammatory compounds, anti-neoplastic agent or analgesics.

The additional therapeutic agent is administered prior to, concomitantly, or subsequent to administration of the PD-1 inhibitor. For example, the PD-1 inhibitor and the additional agent are administered in separate formulations within at least 1, 2, 4, 6, 10, 12, 18, or more than 24 hours apart. Optionally, the additional agent is formulated together with the PD-1 inhibitor. When the additional agent is present in a different composition, different routes of administration may be used. The agent is administered at doses known to be effective for such agent for treating, reducing, or preventing an infection.

Concentrations of the PD-1 inhibitor and the additional agent depends upon different factors, including means of administration, target site, physiological state of the mammal, and other medication administered. Thus treatment dosages may be titrated to optimize safety and efficacy and is within the skill of an artisan. Determination of the proper dosage and administration regime for a particular situation is within the skill of the art.

Optionally, the subject is further administered a vaccine that elicits a protective immune response against the infectious agent that causes a persistent infection. For example, the subject receives a vaccine that elicits an immune response against human immunodeficiency virus (HIV), tuberculosis, influenza, or hepatitis C. Exemplary vaccines are described, for example, in Berzofsky et al. (J. Clin. Invest. 114:456-462, 2004). If desired, the vaccine is administered with a prime-booster shot or with adjuvants.

PD-1 inhibitors are administered in an amount sufficient to increase T cell, e.g., CD8+ T cell, cytotoxicity. An increase in T-cell cytotoxicity results in an increased immune response and a reduction in the persistent infection. An increased immune response is measured, for example, by an increase in immune cell proliferation, e.g., T-cell or B cell, an increase in cytokine production, and an increase in the clearance of an infectious agent. Such reduction includes the alleviation of one or more of symptoms associated with the persistent infection. Administration of the PD-1 inhibitor reduces the persistent infection or alleviates one or more symptoms associated with the persistent infection by at least 10%, 20%, 30%, 40%, 50%, 60%, 70%, 80%, 90%, or 100% as compared to an untreated subject.

Treatment is efficacious if the treatment leads to clinical benefit such as, a reduction of the load of the infectious agent in the subject. When treatment is applied prophylactically, "efficacious" means that the treatment retards or prevents an infection from forming. Efficacy may be determined using any known method for diagnosing or treating the particular infection.

Therapeutic Administration

The invention includes administering to a subject a composition that includes a compound that reduces PD-1 expression or activity (referred to herein as an "PD-1 inhibitor" or "therapeutic compound").

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-infection agents or therapeutic agents for treating, preventing or alleviating a symptom of a particular infection or cancer. A therapeutic regimen is carried out by identifying a mammal, e.g., a human patient suffering from (or at risk of developing) an infection or cancer, using standard methods.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The compound is administered prophylactically, or after the detection of an infection. The compound is optionally formulated as a component of a cocktail of therapeutic drugs to treat infection. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, PD-1 inhibitor is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

Where the therapeutic compound is a nucleic acid encoding a protein, the Therapeutic nucleic acid is administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. Proc Natl Acad Sci USA 88:1864-1868), and the like. Alternatively, a nucleic acid therapeutic is introduced intracellularly and incorporated within host cell DNA for expression, by homologous recombination or remain episomal.

For local administration of DNA, standard gene therapy vectors used. Such vectors include viral vectors, including those derived from replication-defective hepatitis viruses (e.g., HBV and HCV), retroviruses (see, e.g., WO 89/07136; Rosenberg et al., 1990, N. Eng. J. Med. 323(9):570-578), adenovirus (see, e.g., Morsey et al., 1993, J. Cell. Biochem., Supp. 17E), adeno-associated virus (Kotin et al., 1990, Proc. Natl. Acad. Sci. USA 87:2211-2215), replication defective herpes simplex viruses (HSV; Lu et al., 1992, Abstract, page 66, Abstracts of the Meeting on Gene Therapy, September 22-26, Cold Spring Harbor Laboratory, Cold Spring Harbor, N.Y.), and any modified versions of these vectors. The invention may utilize any other delivery system which accomplishes in vivo transfer of nucleic acids into eucaryotic cells. For example, the nucleic acids may be packaged into liposomes, e.g., cationic liposomes (Lipofectin), receptor-mediated delivery systems, non-viral nucleic acid-based vectors, erytbrocyte ghosts, or microspheres (e.g., microparticles; see, e.g., U.S. Pat. No. 4,789,734; 4,925,673; 3,625, 214; Gregoriadis, 1979, Drug Carriers in Biology and Medicine, pp. 287-341 (Academic Press). Naked DNA may also be administered.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle which is suitable for administration to an animal e.g., physiological saline. A therapeutically effective amount is an amount which is capable of producing a medically desirable result, e.g., an decrease of a PD-1 gene product in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. Typically, plasmids are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant adenoviral vectors encoding the PD-1 inhibitor into a mammal may be administered at a concentration of at least $10^5$, $10^6$, $10^7$, $10^8$, $10^9$, $10^{10}$, or $10^{11}$ plaque forming unit (pfu).

PD-1 gene products are administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 moles of the polypeptide of the invention would be administered per kg of body weight per day. The compositions of the invention are useful for parenteral administration, such as intravenous, subcutaneous, intramuscular, and intraperitoneal.

PD-1 inhibitors are effective upon direct contact of the compound with the affected tissue. Accordingly, the compound may be administered topically. Alternatively, PD-1 inhibitors may be administered systemically. Additionally, compounds may be administered by implanting (either directly into an organ (e.g., intestine or liver) or subcutaneously) a solid or resorbable matrix which slowly releases the compound into adjacent and surrounding tissues of the subject. For example, for the treatment of gastrointestinal infection, the compound may be administered systemically (e.g., intravenously, rectally or orally) or locally (e.g., directly into gastric tissue). Alternatively, a PD-1 inhibitor-impregnated wafer or resorbable sponge is placed in direct contact with gastric tissue. The PD-1 inhibitor is slowly released in vivo by diffusion of the drug from the wafer and erosion of the polymer matrix. As another example, infection of the liver (i.e., hepatitis) is treated by infusing into the liver vasculature a solution containing the PD-1 inhibitor.

For the treatment of neurological infections, the PD-1 inhibitor may be administered intravenously or intrathecally (i.e., by direct infusion into the cerebrospinal fluid). For local administration, a compound-impregnated wafer or resorbable sponge is placed in direct contact with CNS tissue. The compound or mixture of compounds is slowly released in vivo by diffusion of the drug from the wafer and erosion of the polymer matrix. Alternatively, the compound is infused into the brain or cerebrospinal fluid using standard methods. For example, a burr hole ring with a catheter for use as an injection port is positioned to engage the skull at a bun hole drilled into the skull. A fluid reservoir connected to the catheter is accessed by a needle or stylet inserted through a septum positioned over the top of the burr hole ring. A catheter assembly (described, for example, in U.S. Pat. No. 5,954,687) provides a fluid flow path suitable for the transfer of fluids to or from selected location at, near or within the brain to allow administration of the drug over a period of time.

For cardiac infections, the compound may be delivered, for example, to the cardiac tissue (i.e., myocardium, pericardium, or endocardium) by direct intracoronary injection through the chest wall or using standard percutaneous catheter based methods under fluoroscopic guidance. Thus, the inhibitor may be directly injected into tissue or may be infused from a stent or catheter which is inserted into a bodily lumen. Any variety of coronary catheter or perfusion catheter may be used to administer the compound. Alternatively, the compound is coated or impregnated on a stent that is placed in a coronary vessel.

Pulmonary infections may be treated, for example, by administering the compound by inhalation. The compounds are delivered in the form of an aerosol spray from a pressured container or dispenser which contains a suitable propellant, e.g., a gas such as carbon dioxide or a nebulizer.

One in the art will understand that the patients treated according to the invention may have been subjected to the same tests to diagnose a persistently infected subject or may have been identified, without examination, as one at high risk due to the presence of one or more risk factors (e.g., exposure to infectious agent, exposure to infected subject, genetic predisposition, or having a pathological condition predisposing to secondary infections). Reduction of persistent infection symptoms or damage may also include, but are not limited to, alleviation of symptoms, diminishment of extent of disease, stabilized (i.e., not worsening) state of disease, delay or slowing of disease progression, and amelioration or palliation of the disease state. Treatment may occur at home with close supervision by the health care provider, or may occur in a health care facility.

Methods to Measure Immune Response

Methods for measuring the immune response following treatment according to the present invention are well known in the art. The activity of T cells may be assessed, for example, by assays that detect cytokine production, assays measuring T cell proliferation, assays that measure the clearance of the microbial agent, and assays that measure CD8+ T cell cytotoxicity. These assays are described, for example, in U.S. Pat. No. 6,808,710 and U.S. Patent Application Publication Nos. 20040137577, 20030232323, 20030166531, 20030064380, 20030044768, 20030039653, 20020164600, 20020160000, 20020110836, 20020107363, and 20020106730, all of which are hereby incorporated by reference.

Optionally, the ability of a PD-1 inhibitor to increase CD8+ T cell cytotoxicity is assessed by assays that measure the proliferation of CD8+ T cells (e.g., thymidine incorporation, BrdU assays, and staining with cell cycle markers (e.g., Ki67 and CFSE), described, for example, by Dong et al (Nature 5:1365-1369, 1999). In one example, T-cell proliferation is monitored by culturing the purified T-cells expressing PD-1 with a PD-1 inhibitor, a primary activation signal as described above, and $^3$H-thymidine. The level of T-cell proliferation is determined by measuring thymidine incorporation.

CD8+ T cell cytotoxicity is also assessed by lysis assays (e.g., 51Cr release assays or assays detecting the release of perforin or granzyme), assays that detect caspase activation, or assays that measure the clearance of the microbial agent from the infected subject. For example, the viral load in a biological sample from the infected subject (e.g., serum, spleen, liver, lung, or the tissue to which the virus is tropic) may be measured before and after treatment.

The production of cytokines such as IFNγ, TNF-α, and IL-2 may also be measured. For example, purified T-cells are cultured in the presence of the PD-1 inhibitor protein and a primary activation signal. The level of various cytokines in the supernatant can be determined by sandwich enzyme-linked immunosorbent assays or other conventional assays described, for example, in Dong et al (Nature 5:1365-1369, 1999).

If desired, the efficacy of the PD-1 inhibitor is assessed by its ability to induce co-stimulation of T cells. For example, a method for in vitro T-cell co-stimulation involves providing purified T-cells that express PD-1 with a first or primary activation signal by anti-CD3 monoclonal antibody or phorbol ester, or by antigen in association with class II MHC. The ability of a candidate compound agent to reduce PD-1 expression or activity and therefore provide the secondary or co-stimulatory signal necessary to modulate immune function, to these T-cells can then be assayed by any one of the several conventional assays well known in the art.

A B cell response is assessed by an antigen specific ELISA (e.g., LCMV, HIV, tuberculosis, or malaria), plasma cell ELISPOT, memory B-cell assay, phenotyping of B cell, and analysis of germinal centers by immunohistochemistry.

Screening Assays

The present invention provides screening methods to identify compounds that can inhibit the expression or activity of PD-1. Useful compounds include any agent that inhibits the biological activity or reduces the cellular level of PD-1. For example, candidate compounds may reduce binding of PD-1 to PD-L1, PD-L2, or both. Using such agents as lead compounds, for example, the present screening methods also allow the identification of further novel, specific inhibitors of PD-1 that function to treat, reduce, or prevent persistent infections, or alternatively, that alleviate one or more symptoms associated with such infections. The method of screening may involve high-throughput techniques.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof. For example, a useful candidate compound according to the present invention reduces binding of PD-1 to PD-L1, PD-L2, or both.

A number of methods are available for carrying out such screening assays. According to one approach, candidate compounds are added at varying concentrations to the culture medium of cells expressing PD-1. By a "PD-1 gene" is meant a nucleic acid that encodes a PD-1 protein. By "PD-1 fusion gene" is meant a PD-1 promoter and/or all or part of a PD-1 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and beta-galactosidase.

Gene expression of PD-1 is then measured, for example, by standard Northern blot analysis (Ausubel et al., supra), using any appropriate fragment prepared from the nucleic acid molecule of PD-1 as a hybridization probe or by real time PCR with appropriate primers. The level of gene expression in the presence of the candidate compound is compared to the level measured in a control culture medium lacking the candidate molecule. If desired, the effect of candidate compounds may, in the alternative, be measured at the level of PD-1 polypeptide using the same general approach and standard immunological techniques, such as Western blotting or immunoprecipitation with an antibody specific to PD-1 for example. For example, immunoassays may be used to detect or monitor the level of PD-1. Polyclonal or monoclonal antibodies which are capable of binding to PD-1 may be used in any standard immunoassay format (e.g., ELISA or RIA assay) to measure the levels of PD-1. PD-1 can also be measured using mass spectroscopy, high performance liquid chromatography, spectrophotometric or fluorometric techniques, or combinations thereof.

Alternatively, the screening methods of the invention may be used to identify candidate compounds that decrease the biological activity of PD-1 by reducing binding of PD-1 to PD-L1, PD-L2, or both by at least 10%, 20%, 30%, 40%, 50%, 60%, 70%, 80%, 90%, 95%, or 100% relative to an untreated control. For example, a candidate compound may be tested for its ability to decrease PD-1 activity in cells that naturally express PD-1, after transfection with cDNA for PD-1, or in cell-free solutions containing PD-1, as described further below. The effect of a candidate compound on the binding or activation of PD-1 can be tested by radioactive and non-radiaoctive binding assays, competition assays, and receptor signaling assays.

As a specific example, mammalian cells (e.g., rodent cells) that express a nucleic acid encoding PD-1 are cultured in the presence of a candidate compound (e.g., a peptide, polypeptide, synthetic organic molecule, naturally occurring organic molecule, nucleic acid molecule, or component thereof). Cells may either endogenously express PD-1 or may alternatively be genetically engineered by any standard technique known in the art (e.g., transfection and viral infection) to overexpress PD-1. The expression level of PD-1 is measured in these cells by means of Western blot analysis and subsequently compared to the level of expression of the same protein in control cells that have not been contacted by the candidate compound. A compound which promotes a decrease in the level of PD-1 activity as a result of reducing its synthesis or biological activity is considered useful in the invention.

In one particular example, a compound that interferes with PD-1 binding to PD-L1, PD-L2, or both (thereby reducing the biological activity of PD-1), leading to an increase in an immune response, is useful according to the present invention. Given its ability to decrease the biological activity of PD-1, such a molecule may be used, for example, as a therapeutic agent to treat, reduce, or prevent a persistent infection, or alternatively, to alleviate one or more symptoms associated with such infections. As a specific example, a candidate compound may be contacted with two proteins, the first protein being a polypeptide substantially identical to PD-1 and the second protein being either PD-L1 or PD-L2 (i.e., a protein that binds the PD-1 polypeptide under conditions that allow binding and that results in a reduced immune response). According to this particular screening method, the interaction between these two proteins is measured following the addition of a candidate compound. A decrease in the binding PD-1 to the second polypeptide following the addition of the candidate compound (relative to such binding in the absence of the compound) identifies the candidate compound as having the ability to inhibit the interaction between the two proteins. Ultimately, the screening assay of the invention may be carried out, for example, in a cell-free system or using a yeast two-hybrid system. If desired, one of the proteins or the candidate compound may be immobilized on a support as described above or may have a detectable group.

Alternatively, or in addition, candidate compounds may be screened for those which specifically bind to and thereby inhibit PD-1. The efficacy of such a candidate compound is dependent upon its ability to interact with PD-1. Such an interaction can be readily assayed using any number of standard binding techniques and functional assays (e.g., those described in Ausubel et al., supra). For example, a candidate compound may be tested in vitro for interaction and binding with PD-1 and its ability to modulate immune responses may be assayed by any standard assays (e.g., those described herein).

For example, a candidate compound that binds to PD-1 may be identified using a chromatography-based technique. For example, a recombinant PD-1 may be purified by standard techniques from cells engineered to express PD-1 (e.g., those described above) and may be immobilized on a column. Alternatively, the naturally-occurring PD-1 may be immobilized on a column. A solution of candidate compounds is then passed through the column, and a compound specific for PD-1 is identified on the basis of its ability to bind to PD-1 and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

Screening for new inhibitors and optimization of lead compounds may be assessed, for example, by assessing their ability to modulate cytotoxic T cell activity or the immune response using standard techniques. In addition, these candidate compounds may be tested for their ability to function as anti-microbial agents (e.g., as described herein). Compounds isolated by this approach may also be used, for example, as therapeutics to treat, reduce, or prevent persistent infections, or alternatively, to alleviate one or more symptoms associated with such infections. Compounds which are identified as binding to PD-1 with an affinity constant less than or equal to 10 mM are considered particularly useful in the invention.

Potential therapeutic agents include organic molecules, peptides, peptide mimetics, polypeptides, and antibodies that bind to a nucleic acid sequence or polypeptide that encodes PD-1 and thereby inhibit or extinguish their activity.

Potential anti-microbial agents also include small molecules that bind to and occupy the binding site of such polypeptides thereby preventing binding to cellular binding molecules, such that normal biological activity is prevented. Other potential anti-microbial agents include antisense molecules.

Diagnostic and Prognostic Methods

Cancer, e.g. angioimmunoblastic T cell lymphoma or Nodular Lymphocyte Predominant Hodgkin's Lymphoma are detected by examining the amount of a PD-1 polypeptide in a test sample (i.e., a patient derived sample). A change in the level if the PD-1 polypeptide compared to a control sample is indicative of cancer in the subject. The change may be an increase or a decrease in the PD-1 polypeptide relative to a control sample. The control sample is prepared (i.e., fractionated) in a similar fashion as the test sample.

A sample is for example, blood, serum, acsites fluid, urine, or other bodily fluids. Preferably the sample is a T-cell or a B-cell The amount of the PD-1 is determined in the test sample and compared to the expression of the normal control level. By normal control level is meant the expression level of a PD-1 polypeptide typically found in a subject not suffering from a cancer. An increase of the level in the patient derived sample of a PD-1 indicates that the subject is suffering from or is at risk of developing cancer. In contrast, when the methods are applied prophylacticly, a similar level or a decrease in the level in the patient derived sample of a PD-1 polypeptide indicates that the subject is not suffering from or is at risk of developing cancer. An increase of the level in the patient derived sample of a PD-1 polypeptide indicates that the subject is suffering from or is at risk of developing cancer.

The alteration in the amount of the PD-1 polypeptide is statistically significant. By statistically significant is meant that the alteration is greater than what might be expected to happen by change alone. Statistical significance is determined by method known in the art. For example statistical significance is determined by p-value. The p-values is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is at least 0.05. Preferably, the p-value is 0.04, 0.03, 0.02, 0.01, 0.005, 0.001 or less.

The "diagnostic accuracy" of a test, assay, or method concerns the ability of the test, assay, or method to distinguish between patients having cancer or at risk for cancer is based on whether the patients have a "clinically significant presence" of a PD-1 polypeptide. By "clinically significant presence" is meant that the presence of the PD-1 polypeptide in the patient (typically in a sample from the patient) is higher or lower than the predetermined cut-off point (or threshold value) for that PD-1 polypeptide and therefore indicates that the patient has cancer for which the sufficiently high presence of that protein is a marker.

The terms "high degree of diagnostic accuracy" and "very high degree of diagnostic accuracy" refer to the test or assay for that PD-1 polypeptide with the predetermined cut-off point correctly (accurately) indicating the presence or absence of the cancer. A perfect test would have perfect accuracy. Thus, for individuals who have diabetes, the test would indicate only positive test results and would not report any of those individuals as being "negative" (there would be no "false negatives"). In other words, the "sensitivity" of the test (the true positive rate) would be 100%. On the other hand, for individuals who did not have diabetes, the test would indicate only negative test results and would not report any of those individuals as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

Changing the cut point or threshold value of a test (or assay) usually changes the sensitivity and specificity but in a qualitatively inverse relationship. For example, if the cut point is lowered, more individuals in the population tested will typically have test results over the cut point or threshold value. Because individuals who have test results above the cut point are reported as having the disease, condition, or syndrome for which the test is being run, lowering the cut point will cause more individuals to be reported as having positive results (i.e., that they have cancer). Thus, a higher proportion of those who have cancer will be indicated by the test to have it. Accordingly, the sensitivity (true positive rate) of the test will be increased. However, at the same time, there will be more false positives because more people who do not have the disease, condition, or syndrome (i.e., people who are truly "negative") will be indicated by the test to have PD-1 polypeptide values above the cut point and therefore to be reported as positive (i.e., to have the disease, condition, or syndrome) rather than being correctly indicated by the test to be negative. Accordingly, the specificity (true negative rate) of the test will be decreased. Similarly, raising the cut point will tend to decrease the sensitivity and increase the specificity. Therefore, in assessing the accuracy and usefulness of a proposed medical test, assay, or method for assessing a patient's condition, one should always take both sensitivity and specificity into account and be mindful of what the cut point is at which the sensitivity and specificity are being reported because sensitivity and specificity may vary significantly over the range of cut points.

There is, however, an indicator that allows representation of the sensitivity and specificity of a test, assay, or method over the entire range of cut points with just a single value. That indicator is derived from a Receiver Operating Characteristics ("ROC") curve for the test, assay, or method in question. See, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Patients With Coronory Artery Disease," Clin. Chem., 1992, 38(8): 1425-1428.

An ROC curve is an x-y plot of sensitivity on the y-axis, on a scale of zero to one (i.e., 100%), against a value equal to one minus specificity on the x-axis, on a scale of zero to one (i.e., 100%). In other words, it is a plot of the true positive rate against the false positive rate for that test, assay, or method. To construct the ROC curve for the test, assay, or method in question, patients are assessed using a perfectly accurate or "gold standard" method that is independent of the test, assay, or method in question to determine whether the patients are truly positive or negative for the disease, condition, or syndrome (for example, coronary angiography is a gold standard test for the presence of coronary atherosclerosis). The patients are also tested using the test, assay, or method in question, and for varying cut points, the patients are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve.

The area under the curve ("AUC") is the indicator that allows representation of the sensitivity and specificity of a test, assay, or method over the entire range of cut points with just a single value. The maximum AUC is one (a perfect test) and the minimum area is one half. The closer the AUC is to one, the better is the accuracy of the test.

By a "high degree of diagnostic accuracy" is meant a test or assay (such as the test of the invention for determining the clinically significant presence of PD-1 polypeptide, which thereby indicates the presence of diabetes) in which the AUC (area under the ROC curve for the test or assay) is at least 0.70, desirably at least 0.75, more desirably at least 0.80, preferably at least 0.85, more preferably at least 0.90, and most preferably at least 0.95.

By a "very high degree of diagnostic accuracy" is meant a test or assay in which the AUC (area under the ROC curve for the test or assay) is at least 0.875, desirably at least 0.90, more desirably at least 0.925, preferably at least 0.95, more preferably at least 0.975, and most preferably at least 0.98.

Optionally, expression of other known biomarkers for a particular cancer are also determined as further indication of whether or not the subject is carrying a cancer. For example, CD10, bcl-6, CD20, CD57 or CXCR5 is detected.

The PD-1 polypeptide and the additional biomarkers are detected in any suitable manner, but are typically detected by contacting a sample from the patient with an antibody which binds the PD-1 or biomarker and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Expression of a PD-1 polypeptide also allows for the course of treatment of cancer to be monitored. In this method, a biological sample is provided from a subject undergoing treatment, e.g., surgical, chemotherapeutic or hormonal treatment, for a cancer. If desired, biological samples are obtained from the subject at various time points before, during, or after treatment. Expression of a PD-1 is then determined and compared to a reference, e.g. control whose cancer state is known. The reference sample has been exposed to the treatment. Alternatively, the reference sample has not been exposed to the treatment. Optionally, such monitoring is carried out preliminary to a second look surgical surveillance procedures and subsequent surgical surveillance procedures. For example, samples may be collected from subjects who have received initial surgical treatment for cancer and subsequent treatment with antineoplastic agents for that cancer to monitor the progress of the treatment.

If the reference sample is from a subject that does not have cancer, a similarity or a decrease in the amount of the PD-1 polypeptide in the test sample and the reference sample indicates that the treatment is efficacious. However, an increase in the amount of the PD-1 polypeptide in the test sample and the reference sample indicates a less favorable clinical outcome or prognosis.

By "efficacious" is meant that the treatment leads to a decrease in the amount of a PD-1 polypeptide, or a decrease in size, prevalence, or metastatic potential of a tumor in a subject. Assessment of cancer is made using standard clinical protocols. Efficacy is determined in association with any known method for diagnosing or treating the particular tumor. Expression of a PD-1 polypeptide also allows the identification of patients who will be responsive to systemic, e.g., chemotherapeutic, hormonal or radiation therapy. In this method, a biological sample is provided from a subject prior to undergoing surgical treatment, for a cancer. Expression of a PD-1 polypeptide is then determined and compared to a biological sample obtained from the subject after surgical removal of the cancer. The patient will likely be responsive to systemic treatment if the amount of the PD-1 polypeptide decreases after surgical removal the cancer. In contrast a the patient will likely not be responsive to systemic treatment if the amount of the polypeptide remains constant or increase after surgical removal of the cancer.

Expression of the PD-1 polypeptide or other cancer biomarkers is determined at the protein or nucleic acid level using any method known in the art. For example, Northern hybridization analysis using probes which specifically recognize one or more of these sequences can be used to determine gene expression. Alternatively, expression is measured using reverse-transcription-based PCR assays, e.g., using primers specific for the differentially expressed sequence of genes. Expression is also determined at the protein level, i.e., by measuring the levels of peptides encoded by the gene products described herein, or activities thereof. Such methods are well known in the art and include, e.g., immunoassays based on antibodies to proteins encoded by the genes. Any biological material can be used for the detection/quantification of the protein or it's activity. Alternatively, a suitable method can be selected to determine the activity of proteins encoded by the marker genes according to the activity of each protein analyzed.

The subject is preferably a mammal. The mammal is, e.g., a human, non-human primate, mouse, rat, dog, cat, horse, or cow. Subjects are typically human females or human males The subject has been previously diagnosed as carrying a cancer, and possibly has already undergone treatment for the cancer. Alternatively, the subject has not been previously diagnosis as carrying a cancer. The present invention is useful with all patients at risk for a cancer. Although each type of cancer has its own set of risk factors, the risk of developing cancer increases as with aged, gender, race and personal and family medical history. Other risk factors are largely related to lifestyle choices, while certain infections, occupational exposures and some environmental factors can also be related to developing cancer.

Diagnosis of cancer is typically made through the identification of a mass on an examination, though it may also be through other means such as a radiological diagnosis, or ultrasound. Treatment is typically through cytoreductive surgery, followed by treatment with antineoplastic agents such as docetaxel, vinorelbine gemcitabine, capecitabine or a combinations of cyclophosphamide, methotrexate, and fluorouracil; cyclophosphamide, doxorubicin, and fluorouracil; doxorubicin and cyclophosphamide; doxorubicin and cyclophosphamide with paclitaxel; doxorubicin followed by CMF; or Cyclophosphamide, epirubicin and fluorouracil. In addition, many patients will require radiation therapy.

Immunoassays carried out in accordance with the present invention may be homogeneous assays or heterogeneous assays. In a homogeneous assay the immunological reaction usually involves the specific antibody (e.g., PD-1 polypeptide), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are radioimmunoassays, immunofluorescence methods, or enzyme-linked immunoassays.

Those skilled in the art will be familiar with numerous specific immunoassay formats and variations thereof, which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label." Antibodies are conjugated to a solid support suitable for a diagnostic assay (e.g., beads, plates, slides or wells formed from materials such as latex or polystyrene) in accordance with known techniques, such as precipitation. Antibodies as described herein may likewise be conjugated to detectable groups such as radiolabels (e.g., 35 S, 125 I, 131 I), enzyme labels (e.g., horseradish peroxidase, alkaline phosphatase), and fluorescent labels (e.g., fluorescein) in accordance with known techniques.

Diagnostic kits for carrying out the methods described herein are produced in a number of ways. In one embodiment, the diagnostic kit comprises (a) an antibody (e.g., PD-1 polypeptide) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) an antibody, and (b) a specific binding partner for the antibody conjugated to a detectable group. Ancillary agents as described above may likewise be included. The test kit may be packaged in any suitable manner, typically with all elements in a single container along with a sheet of printed instructions for carrying out the test. This invention is based in part on the experiments described in the following examples. These examples are provided to illustrate the invention and should not be construed as limiting.

EXAMPLE 1

Inhibition of the PD-1 Pathway in Chronically-Infected Mice Using Anti-PD-L1 Antibodies Mice infected with various strains of the lymphocytic choriomeningitis virus (LCMV) were used to study the effect of chronic viral infection on CD8+ T cell function. The LCMV Armstrong strain causes an acute infection that is cleared within 8 days, leaving behind a long-lived population of highly functional, resting memory CD8+ T cells. The LCMV Cl-13 strain, in contrast, establishes a persistent infection in the host, characterized by a viremia that lasts up to 3 months. The virus remains in some tissues indefinitely and antigen specific CD8+ T cells become functionally impaired. $D^b$NP396-404 CD8+ T cells are physically deleted, while $D^b$GP33-41 and $D^b$GP276-286 CD8+ T cells persist but lose the ability to proliferate or secrete anti-viral cytokines, such as IFN-γ and TNF-α.

C57BL/6 mice were purchased from the National Cancer Institute (Frederick, Md.). Mice were infected i.v. with $2\times10^6$ pfu of LCMV-Cl-13. CD4 depletions were performed by injecting 500 μg of GK1.5 in PBS the day of infection and the day following the infection. LCMV immune mice are generated by infecting mice i.p. with $2\times10^5$ pfu LCMV Armstrong.

Gene array analysis was performed on FACS-purified naïve $D^b$GP33-41 specific P14 transgenic CD8+ T cells, $D^b$GP33-41 specific memory CD8+ T cells derived from LCMV Armstrong immune mice, and $D^b$GP33-41 specific or $D^b$GP276-286 specific CD8+ T cells derived from CD4$^+$ depleted LCMV Cl-13 infected mice. RNA isolation and gene array analysis were performed as described in Kaech et al., (Cell 111:837-51, 2002). PD-1 mRNA was highly expressed in exhausted CD8+ T cells relative to memory CD8+ T cells (FIG. 1A). Furthermore, PD-1 was expressed on the surface of CD8+ T cells in LCMV Cl-13 infected mice, but was not present on the surface of CD8+ T cells after clearance of LCMV Armstrong (FIG. 1B). Chronically infected mice also expressed higher levels of one of the ligands of PD-1, PD-L1, on most lymphocytes and APC compared to uninfected mice. Thus, viral antigen persistence and CD8+ T cell exhaustion are concomitant with an induction in PD-1 expression.

To test the hypothesis that blocking the PD-1/PD-L1 pathway may restore T cell function and enhance viral control during chronic LCMV infection, the PD-1/PD-L1 co-inhibitory pathway was disrupted during chronic LCMV infection using αPD-L1 blocking antibodies. A blocking monoclonal antibody against PD-L1 was administered i.p. every third day to mice infected with LCMV Cl-13 (200 μg of rat anti-mouse PD-L1 IgG2b monoclonal antibodies (clone 10F.5C5 or 10F.9G2)) from day 23 to day 37 post-infection. At day 37, there was approximately 2.5 fold more D$^b$NP396-404 specific CD8+ T cells and 3 fold more D$^b$GP33-41 specific CD8+ T cells in treated mice relative to the untreated controls (FIG. 2A). The induction in proliferation was specific to CD8+ T cells since the number of CD4+ T cells in the spleen were approximately the same in both treated mice and untreated mice (~6×10$^4$ IA$^b$GP61-80 of CD4+ T cells per spleen).

In addition to an increase in CD8+ T cell proliferation, the inhibition of PD-1 signaling also resulted in an increased production of anti-viral cytokines in virus-specific CD8+ T cells. The production of IFN-γ and TNF-α by CD8+ T cells to eight different CTL epitopes was determined. The combined response was 2.3 fold higher in treated mice as compared to untreated mice (FIGS. 2B and 2C). A 2-fold increase in the frequency of TNF-α producing cells was also observed following treatment (FIG. 2D). Viral clearance was also accelerated as the virus was cleared from the serum, spleen, and liver of treated mice. Reduced viral titers were observed in the lung and kidney (~10 fold) by day 37 post-infection (14 days following initiation of treatment) in treated mice. Untreated mice, however, displayed significant levels of virus in all these tissues (FIG. 2E). Viral titers in serum and tissue homogenates were determined using Vero cells, as described in Ahmed et al. (J. Virol. 51:34-41, 1984). The results showing that a PD-1 inhibitor increases CD8+ T cell proliferation and viral clearance therefore indicate that the inhibition of PD-1 signaling restores CD8+ T cell function. Furthermore, inhibition of PD-1 signaling also enhanced B cell responses as the number of LCMV specific antibody secreting cells in the spleen was also increased (>10-fold) following treatment.

CD4$^+$ T cells play a key role in the generation and maintenance of CD8+ T cell responses. In this regard, CD8+ T cells primed in the absence of CD4+ T cell (so-called "helpless" CD8+ T cells) are incapable of mounting normal immune responses. Furthermore, chronic LCMV infection is more severe in the absence of CD4+ T cells. Accordingly, helpless T cells generated during LCMV-Cl-13 infection display an even more profound functional impairment than T cells generated in the presence of CD4+ T cells. D$^b$NP396-404 specific CD8+

T cells are deleted to undetectable levels, and D$^b$GP33-41 and D$^b$GP276-286 CD8+ T cells completely lose the ability to secrete IFN-γ and TNF-α.

Figure 3B:
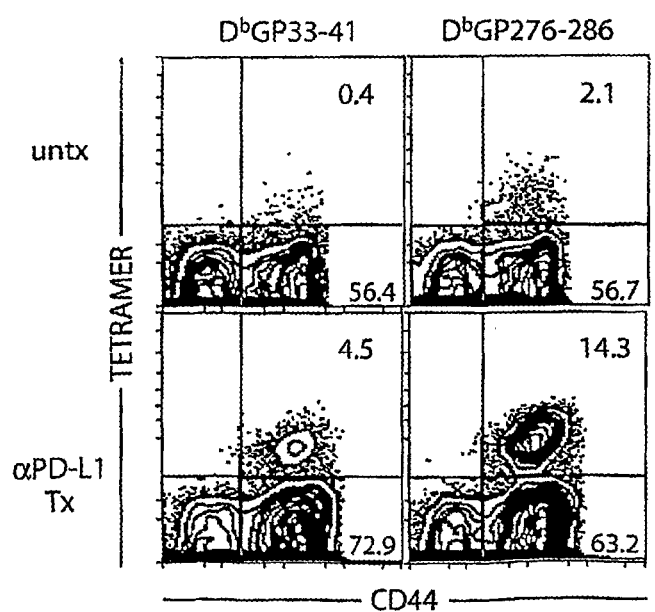
FIG. 3B is a series of images demonstrating the increased frequency of DbGP33-41 and DbGP276-286 specific CD8+ T cells in the spleen of CD4-depleted Cl-13 infected mice treated with anti-PD-L1 (labeled "αPD-L1 Tx") from day 46 to day 60 post-infection versus control (labeled "untx").
Figure 3C:
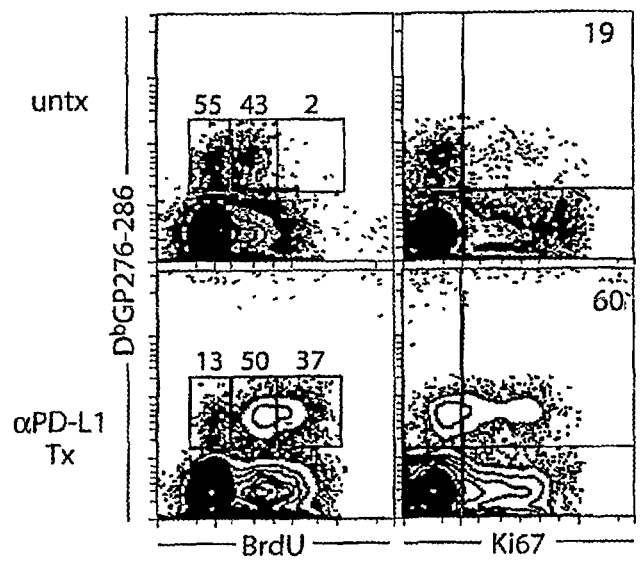
FIG. 3C is a series of images demonstrating increased proliferation of DbGP276-286 specific CD8+ T cells in anti-PD-L1-treated mice, as measured by BrdU incorporation and Ki67 expression.
Figure 3D:
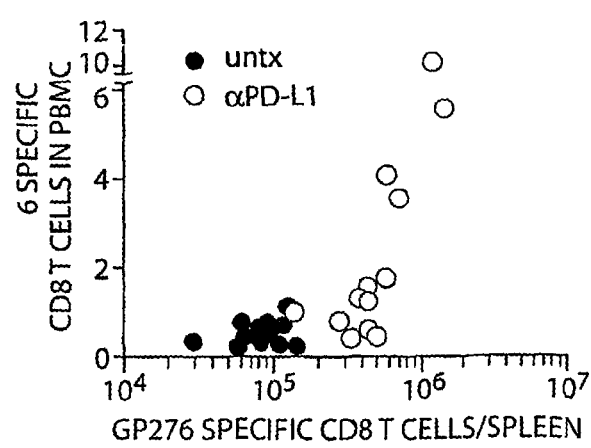
FIG. 3D is a chart showing that mice having high levels of CD8+ T cell expansion demonstrate an appreciable response in peripheral blood mononuclear cells (PBMC), as shown by comparing DbGP276-286 specific CD8+ T cells in the PBMC as compared to DbGP276-286 specific CD8+ T cells in the spleen.

CD4$^+$ T cells were depleted at the time of LCMV-Cl-13 infection and mice were treated with anti-PD-L1 antibodies treatment from day 46 to day 60 post-infection. LCMV-specific CD4+ T cells were not detectable by intracellular IFN-γ staining before or after treatment. Following treatment, treated mice had approximately 7 fold more D$^b$GP276-286 CD8+ T cells and 4 fold more D$^b$GP33-41 CD8$^+$ T cells in their spleen than untreated control mice (FIG. 3A). The number of virus-specific CD8$^+$ T cells in the spleen was also increased (FIG. 3B). This increase in virus-specific CD8$^+$ T cells in treated mice was attributed to an increase in proliferation, as detected by BrdU incorporation. 43% of D$^b$GP276-286 CD8$^+$ T cells incorporated intermediate levels of BrdU and 2% incorporated high levels of BrdU in untreated mice, while 50% D$^b$GP276-286 CD8$^+$ T cells incorporated intermediate levels of BrdU and 37% incorporated high levels of BrdU in treated mice. BrdU analysis was performed by introducing 1 mg/ml BrdU in the drinking water during treatment and staining was performed according to the manufacturer's protocol (BD Biosciences, San Diego, Calif.). Moreover, treated mice contained a higher percentage of CD8$^+$ T cells expressing the cell cycle-associated protein Ki67 (60% versus 19% in untreated mice, FIG. 3C). Response to treatment in CD8$^+$ T cells in the PBMC was restricted to mice having high levels of CD8$^+$ T cell expansion.

PD-1 inhibition also increased anti-viral cytokine production in helpless, exhausted virus-specific CD8$^+$ T cells. Following treatment, the number of D$^b$GP33-41 and D$^b$GP276-286 CD8$^+$ T cells that produce IFN-γ was markedly increased (FIG. 4A), though higher numbers of D$^b$NP396-404, K$^b$NP205-212, D$^b$NP166-175, and D$^b$GP92-101 specific CD8$^+$ T cells were also detected in treated mice (FIG. 4A). 50% of D$^b$GP276-286 specific CD8$^+$ T cells from treated mice can produce IFN-γ compared to the 20% of D$^b$GP276-286 specific CD8$^+$ T cells in control untreated mice. (FIG. 4B). Levels of IFN-γ and TNF-α produced by D$^b$GP276-286 specific CD8+ T cells from treated mice, however, were lower than fully functional D$^b$GP276-286 specific memory cells. (FIG. 4C).

PD-1 inhibition also increased the lytic activity of helpless, exhausted virus-specific CD8$^+$ T cells. Ex vivo lytic activity of virus-specific CD8$^+$ T cells was detected following treatment, using a $^{51}$Cr release assay (Wherry et al., 2003. J. Virol. 77:4911-27). Viral titers were reduced by approximately 3 fold in the spleen, 4 fold in the liver, 2 fold in the lung, and 2 fold in serum after 2 weeks of treatment relative to untreated mice. (FIG. 4E).

These results therefore demonstrate that blocking the PD-1 pathway breaks CTL peripheral tolerance to a chronic viral infection, and that exhausted CD8$^+$ T cells deprived of CD4$^+$ T cell help are not irreversibly inactivated.

EXAMPLE 2

Administration of Anti-Viral Vaccine and PD-1 Inhibitor

One approach for boosting T cell responses during a persistent infection is therapeutic vaccination. The rationale for this approach is that endogenous antigens may not be presented in an optimal or immunogenic manner during chronic viral infection and that providing antigen in the form of a vaccine may provide a more effective stimulus for virus-specific T and B cells. Using the chronic LCMV model, mice were administered a recombinant vaccinia virus expressing the LCMV GP33 epitope as a therapeutic vaccine (VVGP33), which resulted in a modest enhancement of CD8+ T cell responses in some chronically infected mice Four out of the nine chronically infected mice that received the therapeutic vaccine showed a positive response while none of the control mice had a significant increase in the immune response against GP33. When this therapeutic vaccination was combined with a PD-L1 inhibitor, LCMV specific T cell responses were boosted to a greater level than compared to either treatment alone and the effect of combined treatment was more than additive.

EXAMPLE 3

Inhibition of the PD-1 Pathway in Chronically-Infected Mice Using PD-1 RNAi

RNA interference (RNAi) is capable of silencing gene expression in mammalian cells. Long double stranded RNAS (dsRNAs) are introduced into cells and are next processed into smaller, silencing RNAs (siRNAs) that target specific mRNA molecules or a small group of mRNAs. This technology is particularly useful in situations where antibodies are not functional. For example, RNAi may be employed in a situation in which unique splice variants produce soluble forms of PD-1 and CTLA-4.

PD-1 silencer RNAs are inserted into a commercially available siRNA expression vector, such as pSilencer™ expression vectors or adenoviral vectors (Ambion, Austin, Tex.). These vectors are then contacted with target exhausted T cells in vivo or ex vivo (See, Example 4)

EXAMPLE 4

Ex Vivo Rejuvenation of Exhausted T Cells

Virus-specific exhausted CD8$^+$ T cells are isolated from LCMV-Cl-13 chronically infected mice using magnetic beads or density centrifugation. Transfected CD8$^+$ T cells are contacted with a monoclonal antibody that targets PD-L1, PD-L2 or PD-1. As described in Example 1, inhibition of the PD-1 pathway results in the rejuvenation of the CD8$^+$ T cells. Accordingly, there is an increase in CD8$^+$ T cell proliferation and cytokine production, for example. These rejuvenated CD8$^+$ T cells are reintroduced into the infected mice and viral load is measured as described in Example 1.

EXAMPLE 5

In Vitro Screening of Novel CD8$^+$ T Cell Rejuvenator Compounds

Compounds that modulate the PD-1 pathway can be identified in in vivo and ex vivo screening assays based on their ability to reverse CD8$^+$ T cell exhaustion resulting from chronic viral infection.

Exhausted CD8$^+$ T cells are derived from mice chronically infected with LCMV-Cl-13 and next contacted with a test compound. The amount of anti-viral cytokines (e.g., IFN-$\gamma$ or TNF-$\alpha$) released from the contacted T cell is measured, for example, by ELISA or other quantitative method, and compared to the amount, if any, of the anti-viral cytokine released from the exhausted T cell not contacted with the test compound. An increase in the amount of anti-viral cytokine released by treated cells relative to such amount in untreated cells identifies the compound as a PD-1 inhibitor, useful to modulate T cell activity.

EXAMPLE 6

In Vivo Screening of Novel CD8+ T Cell Rejuvenator Compounds

Exhausted CD8+ T cells are derived from mice chronically infected with LCMV-Cl-13. A test compound is administered intravenously to the infected mice. The amount of anti-viral cytokines (e.g., IFN-$\gamma$ or TNF-$\alpha$) that is released into the serum of treated and untreated mice is measured, for example, by ELISA or other quantitative method, and compared. An increase in the amount of anti-viral cytokine found in the serum in treated mice relative to such amount in untreated mice identifies the test compound as a PD-1 inhibitor. Alternatively, the viral titer (e.g., serum viral titer) can be determined prior and subsequent to treatment of the test compound.

EXAMPLE 7

Chimpanzees as a Model for Immunotherapy of Persistent HCV Infection

Chimpanzees provide a model of HCV persistence in humans. Defects in T cell immunity leading to life-long virus persistence both include a deficit in HCV-specific CD4+ T helper cells and impaired or altered CD8+ T effector cell activity. Persistently infected chimpanzees are treated with antibodies against CTLA-4, PD-1, or a combination of the two. The efficacy of blockade of the inhibitory pathways, combined with vaccination using recombinant structural and non-structural HCV proteins, and whether such strategies can enhance the frequency and longevity of virus-specific memory T cells are determined. The defect in T cell immunity is exclusively HCV-specific in persistently infected humans and chimpanzees. The blood and liver of infected chimpanzees are examined for expression of CTLA-4, PD-1, BTLA and their ligands and for the presence of Treg cells. Antiviral activity may then be restored by delivering to chimpanzees humanized monoclonal antibodies that block signaling through these molecules.

Persistently infected chimpanzees are treated with humanized $\alpha$CTLA-4 antibodies (MDX-010, Medarex) or $\alpha$PD-1 antibodies. The initial dose of MDX-010 is 0.3 mg/kg followed 2 weeks later by 1.0 mg/kg and then 3, 10, 30 mg/kg at three week intervals. After treatment with antibodies to co-inhibitory molecules, the humoral and cellular immune responses as well as the HCV RNA load will be determined. Samples are collected at weeks 1, 2, 3, 5, and 8, and then at monthly intervals. Samples include: 1) serum for analysis of transaminases, autoantibodies, neutralizing antibodies to HCV, and cytokine responses, 2) plasma for viral load and genome evolution, 3) PBMC for in vitro measures of immunity, costimulatory/inhibitory receptor expression and function, 4) fresh (unfixed) liver for isolation of intrahepatic lymphocytes and RNA, and 5) fixed (formalin/paraffin embedded) liver for histology and immunohistochemical analysis. Regional lymph nodes are also collected at 2 or 3 time points to assess expression of co-inhibitory molecules and splice variants by immunohistochemistry and molecular techniques. Assays to evaluate the efficacy and safety of these therapies safety will be performed as described herein.

To determine if vaccination with HCV antigens potentiates the therapeutic effect of antibodies to PD-1, chimpazees are treated as follows: 1) intramuscular immunization with recombinant envelope glycoproteins E1 and E2 (in MF59 adjuvant) and other proteins (core plus NS 3, 4, and 5 formulated with ISCOMS) at weeks 0, 4, and 24; 2) intramuscular immunization with the vaccine used in 1) but co-administered with $\alpha$CTLA-4 antibodies (30 mg of each/Kg body weight, intravenously at weeks 0, 4, and 24 when vaccine is given); 3) identical to 2) except that $\alpha$PD-1 (or BTLA) antibodies are substituted for the CTLA-4 antibodies; 4) identical to Groups 2 and 3 except that a combination of CTLA-4 and PD-1 (or BTLA) antibodies are used in addition to the vaccine. HCV-specific T and B cell responses are monitored at monthly intervals after immunization for a period of 1 year.

Markers examined on HCV-tetramer+ and total T cells in this analysis include markers of differentiation (e.g. CD45RA/RO, CD62L, CCR7, and CD27), activation (e.g. CD25, CD69, CD38, and HLA-DR), survival/proliferation (e.g. bcl-2 and Ki67), cytotoxic potential (e.g. granzymes and perforin), and cytokine receptors (CD122 and CD127). An interesting correlation exists between pre-therapy levels of the chemokine IP-10 and response to PEG IFN-$\gamma$/ribavirin. IP-10 levels are measured to investigate a potential correlation between negative regulatory pathways or HCV-specific T cell responses and IP-10 levels. Expression of inhibitory receptors and ligands on PBMC are performed by flow cytometry.

EXAMPLE 8

PD-1 Immunostaining in Reactive Lymphoid Tissue

Materials

Case material was obtained from the Brigham & Women's Hospital, Boston, Mass., in accordance with institutional policies. All diagnoses were based on the histologic and immunophenotypic features described in the World Health Organization Lymphoma Classification system (Jaffe E S, et al. 2001) and in all cases diagnostic material was reviewed by a hematopathologist.

Immunostaining

Immunostaining for PD-1 was performed on formalin-fixed paraffin embedded tissue sections following microwave antigen retrieval in 10 mM citrate buffer, pH 6.0 with a previously described anti-human PD-1 monoclonal antibody (2H7; 5), using a standard indirect avidin-biotin horseradish peroxidase method and diaminobenzidine color development, as previously described (Jones D, et al. 1999; Dorfman D M, et al. 2003). Cases were regarded as immunoreactive for PD-1 if at least 25% of neoplastic cells exhibited positive staining. PD-1 staining was compared with that of mouse IgG isotype control antibody diluted to identical protein concentration for all cases studied, to confirm staining specificity.

Monoclonal antibody 2H7 for PD-1 was used to stain formalin-fixed, paraffin-embedded specimens of reactive lymphoid tissue, thymus, and a range of cases of B cell and T cell lymphoproliferative disorders. In specimens of tonsil exhibiting reactive changes, including follicular hyperplasia, a subset of predominantly small lymphocytes in the germinal centers exhibited cytoplasmic staining for PD-1, with infrequent PD-1-positive cells seen in the interfollicular T cell zones. The PD-1 staining pattern in germinal centers was virtually identical to that seen with an antibody to CD3, a pan-T cell marker, whereas an antibody to CD20, a pan-B cell marker, stained the vast majority of germinal center B cells. Similar results were seen in histologic sections of reactive lymph node and spleen. No PD-1 staining was observed in adult thymus.

EXAMPLE 9

PD-1 Immunostaining in Paraffin Embedded Tissue Sections of B Cell and T Cell Lymphoproliferative Disorders A range of B cell and T cell lymphoproliferative disorders for PD-1 expression were studied; the results are summarized in Table 1. Forty-two cases of B cell lymphoproliferative disorders were examined for PD-1 expression, including representative cases of precursor B lymphoblastic leukemia/lymphoblastic lymphoma, as well as a range of lymphoproliferative disorders of mature B cells, including a number of B cell non-Hodgkin lymphomas of follicular origin, including 6 cases of follicular lymphoma and 7 cases of Burkitt lymphoma. None of the B cell lymphoproliferative disorders showed staining for PD-1. In some cases, non-neoplastic reactive lymphoid tissue was present, and showed a PD-1 staining pattern as seen in tonsil and other reactive lymphoid tissue noted above.

Similarly, in 25 cases of Hodgkin lymphoma, including 11 cases of classical Hodgkin lymphoma and 14 case of lymphocyte predominant Hodgkin lymphoma, the neoplastic cells did not exhibit staining for PD-1. Interestingly, in all 14 cases of lymphocyte predominant Hodgkin lymphoma, the T cells surrounding neoplastic CD20-positive L&H cells were immunoreactive for PD-1, similar to the staining pattern noted for CD57+ T cells in lymphocyte predominant Hodgkin lymphoma. These PD-1-positive cells were a subset of the total CD3+ T cell population present.

A range of T cell lymphoproliferative disorders were studied for expression of PD-1; the results are summarized in Table 1. Cases of precursor T cell lymphoblastic leukemia/lymphoblastic lymphoma, a neoplasm of immature T cells of immature T cells, were negative for PD-1, as were neoplasms of peripheral, post-thymic T cells, including cases of T cell prolymphocytic leukemia, peripheral T cell lymphoma, unspecified, anaplastic large cell lymphoma, and adult T cell leukemia/lymphoma. In contrast, all 19 cases of angioimmunoblastic lymphoma contained foci of PD-1-positive cells that were also immunoreactive for pan-T cell markers such as CD3. PD-1-positive cells were consistently found at foci of expanded CD21+ follicular dendritic cells (FDC) networks, a characteristic feature of angioimmunoblastic lymphoma.

TABLE 1

PD-1 immunostaining in lymphoproliferative disorders.

|  | PD-1 immunostaining |
| --- | --- |
| B cell LPDs | 0/42* |
| B-LL/LL | 0/3 |
| CLL | 0/4 |
| MCL | 0/4 |
| FL | 0/6 |
| MZL | 0/3 |
| HCL | 0/3 |
| DLBCL | 0/6 |
| BL | 0/7 |
| LPL | 0/3 |
| MM | 0/3 |
| Hodgkin lymphoma | 0/25 |
| Classical | 0/11 |
| Nodular lymphocyte predominant | 0/14** |
| T cell LPDs | 18/55 |
| T-LL/LL | 0/5 |
| T-PLL | 0/3 |
| AIL | 19/19 |
| PTCL, unspecified | 0/14 |
| ALCL | 0/12 |
| ATLL | 0/3 |

Abbreviations: B-LL/LL—precursor B cell lymphoblastic lymphoma/lymphoblastic leukemia; CLL—chronic lymphocytic leukemia; MCL—mantle cell lymphoma; FL—follicular lymphoma; MZL—marginal zone lymphoma; HCL—hairy cell leukemia; DLBCL—diffuse large B cell lymphoma; BL—Burkitt lymphoma; LPL—lymphoplasmacytic lymphoma; MM—multiple myeloma; T-LL/L—precursor T lymphoblastic leukemia/lymphoblastic lymphoma; T-PLL—T cell prolymphocytic leukemia; AIL—angioimmunoblastic lymphoma; PTCL—peripheral T cell lymphoma, unspecified; ALCL—anaplastic large cell lymphoma; ATLL—adult T cell leukemia/lymphoma.
*number of immunoreactive cases/total number of cases
**PD-1-positive cells form rosettes around neoplastic L&H cells in 14/14 cases

EXAMPLE 10

General Methods for Studying PD-1 Expression on HIV-Specific Human CD8 T Cells The following methods were used to perform the experiments detailed inn Examples 11-14.

Study Subjects

Study participants with chronic Glade C HIV-1 infection were recruited from outpatient clinics at McCord Hospital, Durban, South Africa, and St. Mary's Hospital, Mariannhill, South Africa. Peripheral blood was obtained from 65 subjects in this cohort, all of whom were antiretroviral therapy naïve at the time of analysis. Subjects were selected for inclusion based on their expressed HLA alleles matching the ten class I tetramers that were constructed (see below). The median viral load of the cohort was 42,800 HIV-1 RNA copies/ml plasma (range 163-750,000), and the median absolute CD4 count was 362 (range 129-1179). Information regarding duration of infection was not available. All subjects gave written informed consent for the study, which was approved by local institutional review boards.

Construction of PD-1 and PD-L1 Antibodies

Monoclonal antibodies to human PD-L1 (29E.2A3, mouse IgG2b) and PD-1 (EH12, mouse IgG1) were prepared as previously described and have been shown to block the PD-1:PD-L1 interaction.

MHC Class I Tetramers

Ten HIV MHC Class I tetramers, synthesized as previously described (Altman J D, et al. 1996), were used for this study: A*0205 GL9 (p24, GAFDLSFFL; SEQ ID NO:1), A*3002 KIY9 (Integrase, KIQNFRVYY; SEQ ID NO:2), B*0801 DI8 (p24, DIYKRWII; SEQ ID NO:3), B*0801 FL8 (Nef, FLKEKGGL; SEQ ID NO:4), B*4201 RM9 (Nef, RPQVPLRPM; SEQ ID NO:5), B*4201 TL9 (p24, TPQDLNTML; SEQ ID NO:6), B*4201 TL10 (Nef, TPGPGVRYPL; SEQ ID NO:7), B*4201 YL9 (RT, YPGIKVKQL; SEQ ID NO:8), B*8101 TL9 (p24, TPQDLNTML; SEQ ID NO:9), and Cw0304 YL9 (p24, YVDRFFKTL; SEQ ID NO:10). The plasmid constructs expressing A*0205, A*3002, and Cw*0304 were kindly provided by Drs. Eugene Ravkov and John Altman, NIH Tetramer Core Facility, Atlanta, Ga.

HLA Class I Tetramer Staining and Phenotypic Analysis

Freshly isolated peripheral blood mononuclear cells (PBMC, 0.5 million) were stained with tetramer for 20 minutes at 37° C. The cells were then washed once with phosphate buffered saline (PBS), pelleted, and stained directly with fluorescein isothiosyanate (FITC)-conjugated anti-CD8 (Becton Dickinson), phycoerythrin-conjugated anti-PD-1 (clone EH12), and ViaProbe (Becton Dickinson). Cells were incubated for 20 minutes at room temperature, washed once in PBS, and resuspended in 200 µl PBS with 1% paraformaldehyde and acquired on a fluorescence-activated cell sorter (FACSCalibur, Becton Dickinson). A minimum of 100,000 events were acquired on the FACSCalibur.

CFSE Proliferation Assays

One million freshly isolated PBMC were washed twice in PBS, pelleted, and resuspended in 1 ml of 0.5 µM carboxyfluorescein diacetate, succinimidyl ester (CFSE, Molecular Probes) for 7 minutes at 37° C. The cells were washed twice in PBS, resuspended in 1 ml R10 medium (RPMI 1640 supplemented with glutiathione, penicillin, streptomycin, and 10% fetal calf serum [FCS]), and plated into one well of a 24-well plate. Initial studies revealed that a final concentration of 0.2 µg/ml peptide yielded optimal proliferative responses, therefore this was the final peptide concentration in the well used for each assay. Negative control wells consisted of PBMC in medium alone, or PBMC in medium with purified anti-PD-L1 (10 µg/ml), and positive control wells were stimulated with 10 µg/ml of phytohemagluttinin (PHA). Following 6-day incubation in a 37° C. incubator, the cells were washed with 2 ml PBS and stained with PE-conjugated MHC Class I tetramers, ViaProbe (Becton Dickinson), and anti-CD8-APC antibodies. Cells were acquired on a FACSCalibur and analyzed by CellQuest® software (Becton Dickinson). Cells were gated on ViaProbe$^-$ CD8$^+$ lymphocytes. The fold increase in tetramer cells was calculated by dividing the percentage of CD8$^+$ tetramer cells in the presence of peptide by the percentage of CD8$^+$ tetramer cells in the absence of peptide stimulation.

Statistical Analysis

Spearman correlation, Mann-Whitney test, and paired t-test analyses were performed using GraphPad Prism Version 4.0a. All tests were 2-tailed and p values of p<0.05 were considered significant.

EXAMPLE 11

PD-1 Expression on HIV-Specific CD8 T Cells

Figure 5A:
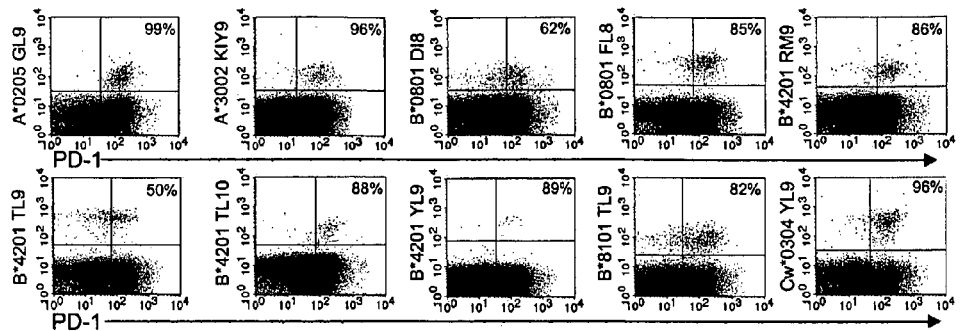
FIG. 5A is a series of images of a flow cytometry experiment showing PD-1 surface expression using 10 HIV tetramers specific for dominant epitopes targeted in chronic Glade C HIV infection. The percentages indicate the percentage of tetramer$^+$ cells that are PD-1$^+$.
Figure 5B:
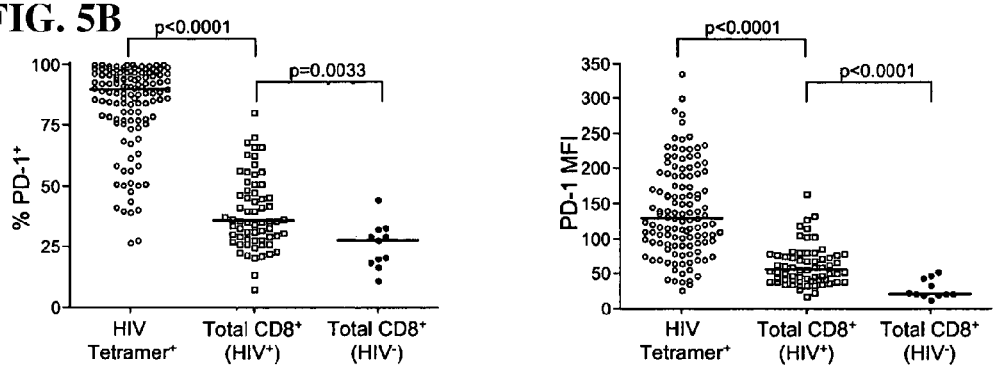
FIG. 5B is a series of charts demonstrating that the percentage and MFI of PD-1 is significantly upregulated on HIV-specific CD8 T cells compared to the total CD8 T cell population ($p<0.0001$) in antiretroviral therapy naïve individuals, and PD-1 is increased on the total CD8 T cell population in HIV-infected versus HIV-seronegative controls ($p=0.0033$ and $p<0.0001$, respectively). 120 HIV tetramer stains from 65 HIV-infected individuals and 11 HIV seronegative controls were included in the analysis.
Figure 5C:
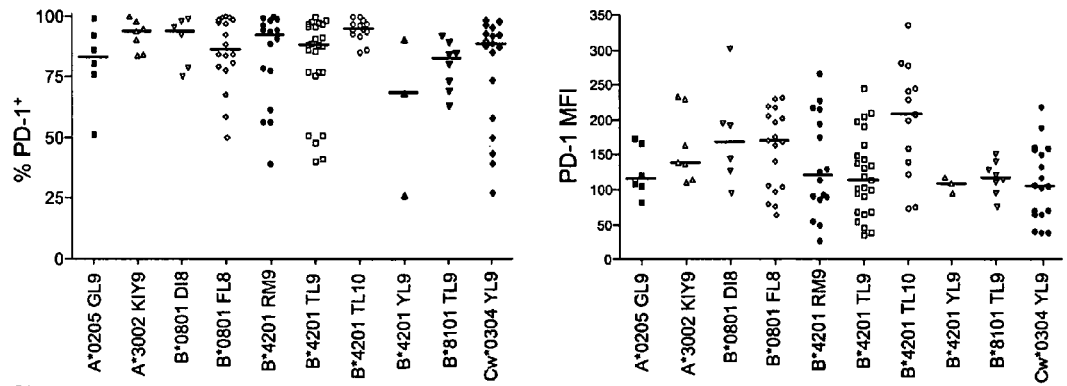
FIG. 5C is a series of charts showing the median percentage and MFI of PD-1 expression on tetramer$^+$ cells by epitope specificity.

A panel of 10 MHC Class I tetramers specific for dominant HIV-1 Glade C virus CD8 T cell epitopes was synthesized, based on prevalent HLA alleles and frequently targeted epitopes in Gag, Nef, Integrase, and RT (Kiepiela P, et al. 2004), allowing direct visualization of surface PD-1 expression on these cells. High resolution HLA typing was performed on the entire cohort, and a subset of 65 antiretroviral therapy naive persons was selected for study based on expression of relevant HLA alleles. A total of 120 individual epitopes were examined, and representative ex vivo staining of PD-1 on HIV tetramer$^+$ cells is shown in FIG. 5A. PD-1 expression was readily apparent on these tetramer$^+$ cells, and was significantly higher than in the total CD8 T cell population from the same individuals (p<0.0001); in turn, PD-1 expression on both tetramer$^+$ CD8 T cells and the total CD8 T cell population was significantly higher than in HIV-seronegative controls (FIG. 5B). For eight of the ten tetramers tested at least one person was identified in whom the level of expression on antigen-specific CD8 cells was 100% (FIG. 5C). PBMC from 3 to 25 individuals were stained for each HIV tetramer response, with median PD-1 expression levels ranging from 68% to 94% of tetramer$^+$ cells (FIG. 5C). These findings were further confirmed by analysis of the mean fluorescence intensity (MFI) of PD-1 on both tetramer$^+$ cells and the total CD8 T cell population (FIG. 5B,C).

Figure 5D:
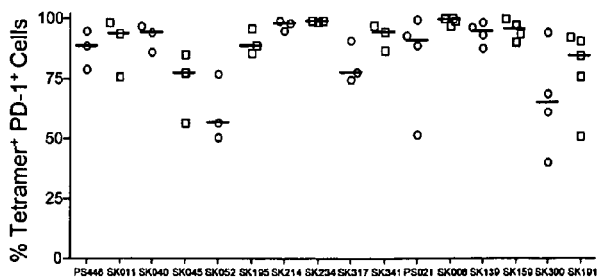
FIG. 5D is a chart depicting the variation in the percentage of PD-1$^+$ cells on different epitope-specific populations within individuals with multiple detectable responses. Horizontal bars indicate the median percentage of PD-1$^+$ HIV tetramer$^+$ cells in each individual.

It was next determined whether there was evidence for epitope-specific differences in terms of PD-1 expression levels in persons with multiple detectable responses. Of the 65 persons examined, 16 individuals had between 3 and 5 tetramer positive responses each. PD-1 expression was nearly identical and approaching 100% for each response analyzed for three of the sixteen subjects; however, the other 13 individuals displayed different patterns of PD-1 expression depending on the epitope (FIG. 5D). These data indicate that PD-1 expression may be differentially expressed on contemporaneous epitope-specific CD8 T cells from a single person, perhaps consistent with recent data indicating epitope-specific differences in antiviral efficacy (Tsomides T J, et al. 1994; Yang O, et al. 1996; Loffredo J T, et al. 2005).

EXAMPLE 12

The Relationship Between PD-1 Expression and HIV Disease Progression

Figure 6A:
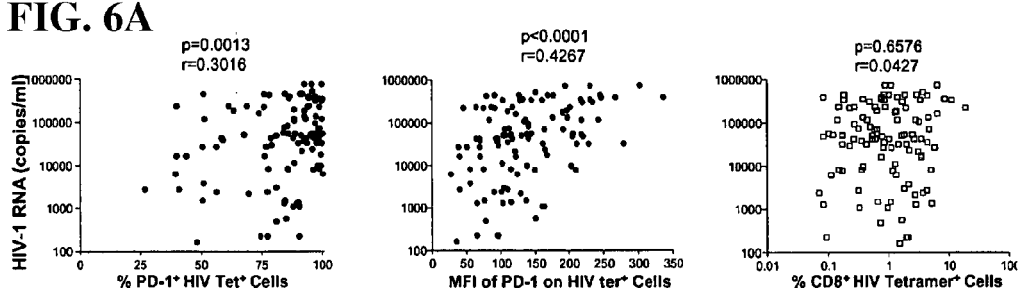
FIG. 6A is a series of charts demonstrating that there is no correlation between the number of HIV-specific CD8 T cells, as measured by tetramer staining, and plasma viral load, whereas there is a positive correlation between both the percentage and MFI of PD-1 on tetramer$^+$ cells and plasma viral load ($p=0.0013$ and $p<0.0001$, respectively).
Figure 6B:
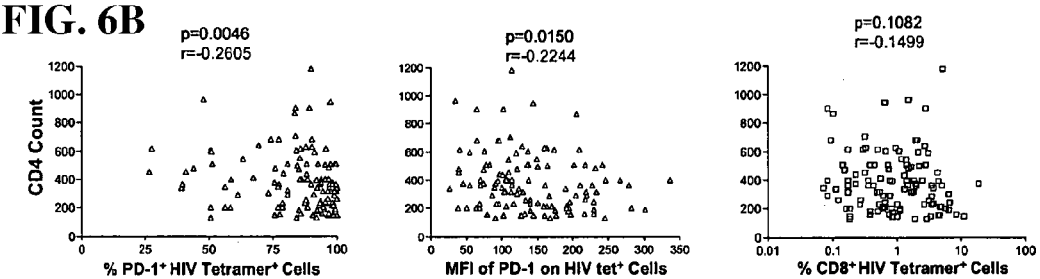
FIG. 6B is a series of charts showing that there is no correlation between the number of HIV tetramer$^+$ cells and CD4 count, whereas there is an inverse correlation between the percentage and MFI of PD-1 on HIV tetramer$^+$ cells and CD4 count ($p=0.0046$ and $p=0.0150$, respectively).
Figure 6C:
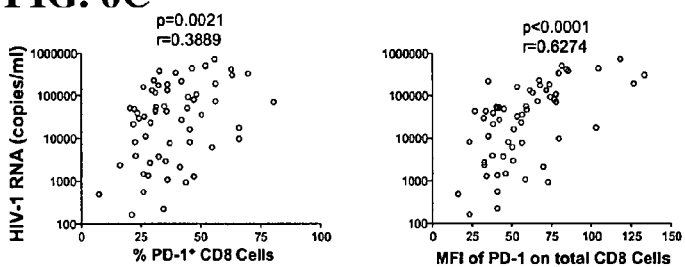
FIG. 6C is a series of charts demonstrating that the percentage and MFI of PD-1 on the total CD8 T cell population positively correlate with plasma viral load ($p=0.0021$ and $p<0.0001$, respectively).
Figure 6D:
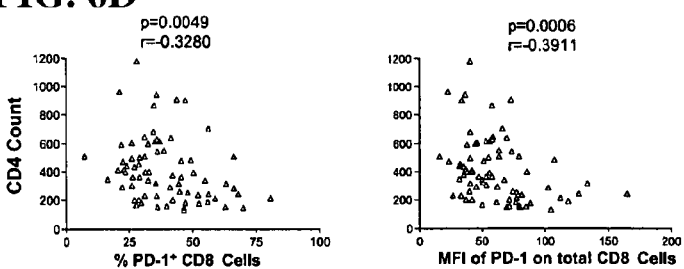
FIG. 6D is a series of charts depicting the percentage and MFI of PD-1 expression on the total CD8 T cell population is inversely correlated with CD4 count ($p=0.0049$ and $p=0.0006$, respectively).

The relationship was determined between PD-1 expression on HIV-specific CD8 T cells and plasma viral load and CD4 counts, both of which are predictors of HIV disease progression. Consistent with previous studies, the relationship between the number of tetramer positive cells and viral load or CD4 count failed to show any significant correlation (FIG. 6A, B). In contrast, there were significant positive correlations with viral load and both the percentage and MFI of PD-1 expression on HIV tetramer positive cells (p=0.0013 and p<0.0001, respectively; FIG. 6A). There were also inverse correlations between CD4 count and both the percentage and MFI of PD-1 on HIV tetramer positive cells (p=0.0046 and p=0.0150, respectively; FIG. 6B). Since the tetramers tested likely represent only a fraction of the HIV-specific CD8 T cell population in these subjects, the relationship between PD-1 expression on all CD8 cells and these parameters was also examined. There were significant positive correlations between viral load and both the percentage and MFI of PD-1 expression on the total CD8 T cell population (p=0.0021 and p<0.0001, respectively; FIG. 6C), and inverse correlations were also observed between CD4 count and both the percentage and MFI of PD-1 expression on the total CD8 T cell population (p=0.0049 and p=0.0006, respectively; FIG. 6D). In this same group, PD-1 expression on CMV-specific CD8 T cells was tested in 5 subjects, and significantly less PD-1 was expressed on these cells compared to HIV-specific CD8 T cells (median 23% CMV tetramer$^+$ PD-1$^+$, p=0.0036, data not shown), and was not different than bulk CD8 T cells in these same individuals, indicating that high PD-1 expression is not a uniform feature of all virus-specific CD8 T cells. These data suggest increasing amounts of antigen in chronic HIV infection result in increased expression of PD-1 on CD8 T cells, and are consistent with murine data in chronic LCMV infection, in which PD-1 expression is associated with functional exhaustion of CD8 T cells (Barber D L, et al. 2005). Moreover, they provide the first clear association, in a large study including analysis of multiple epitopes, between HIV-specific CD8 T cells and either viral load or CD4 count.

EXAMPLE 13

Figure 7A:
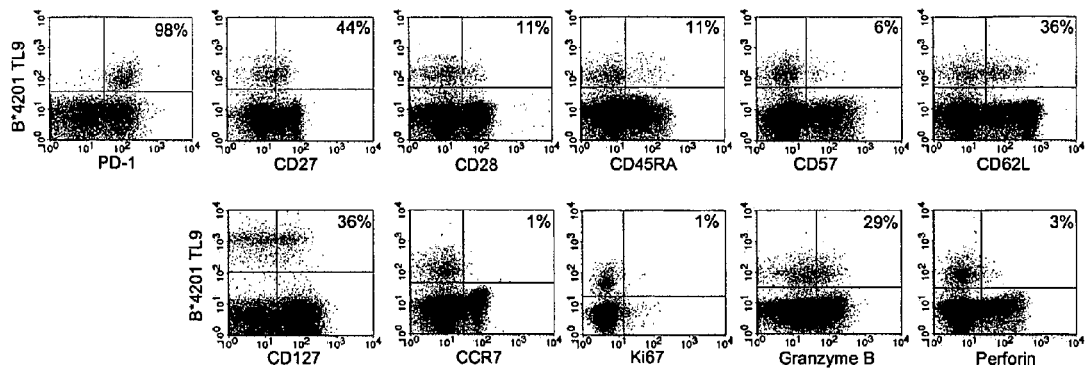
FIG. 7A is a series of images of a flow cytometry experiment showing representative phenotypic staining of B*4201 TL9-specific CD8 T cells from subject SK222 in whom 98% of B*4201 TL9-specific CD8 T cells are PD-1+.
Figure 7B:
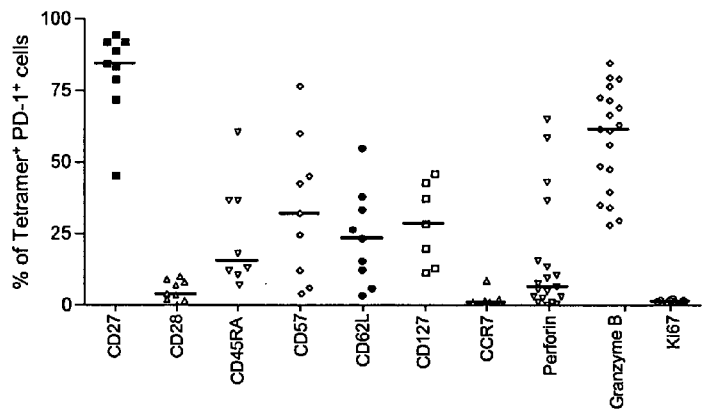
FIG. 7B is a chart illustrating a summary of phenotypic data from persons in whom >95% of HIV-specific CD8 T cells are PD-1+. 7 to 19 samples were analyzed for each of the indicated phenotypic markers. The horizontal bar indicates median percentage of tetramer+PD-1+ cells that were positive for the indicated marker.

The Relationship Between PD-1 Expression and CD8 T Cell Memory Status and Function PD-1 expression was next analyzed in the context of a number of additional phenotypic markers associated with CD8 T cell memory status and function, including CD27, CD28, CD45RA, CD57, CD62L, CD127, CCR7, perforin, granzyme B, and Ki67 (FIG. 7). Representative stainings for these markers on B*4201 TL9 tetramer$^+$ cells from one individual are shown in FIG. 7A, and aggregate data for 13 subjects are shown in FIG. 7B. These studies were limited to those tetramer responses that were greater than 95% PD-1 positive, as multiparameter flow cytometry of greater than 4 colors was not available in KwaZulu Natal. The HIV tetramer+PD-1$^+$ cells express high levels of CD27 and granzyme B, very low levels of CD28, CCR7, and intracellular Ki67, low levels of CD45RA and perforin, and intermediate levels of CD57 and CD62L (FIG. 7B). These data indicate that HIV-specific PD-1$^+$ T cells display an effector/effector memory phenotype, and are consistent with previous reports of skewed maturation of HIV-specific CD8 T cells (Champagne P, et al. 2001; Appay V, et al. 2002; Hess C, et al. 2004). In addition, virus sequencing was performed to determine whether these cells were driving immune escape (Brown J A, et al. 2003). Of 45 of these tetramer-positive responses evaluated, the viral epitopes in only 5 were different from the South African Clade C consensus sequence (data not shown), indicating these cells exert little selection pressure in vivo.

Previous experiments in mice using the LCMV model showed that in vivo blockade of PD-1/PD-L1 interaction by infusion of anti-PD-L1 blocking antibody results in enhanced functionality of LCMV-specific CD8 T cells as measured by cytokine production, killing capacity, proliferative capacity, and, most strikingly, reduction in viral load (Barber D L, et al. 2005).

EXAMPLE 14

Figure 8A:
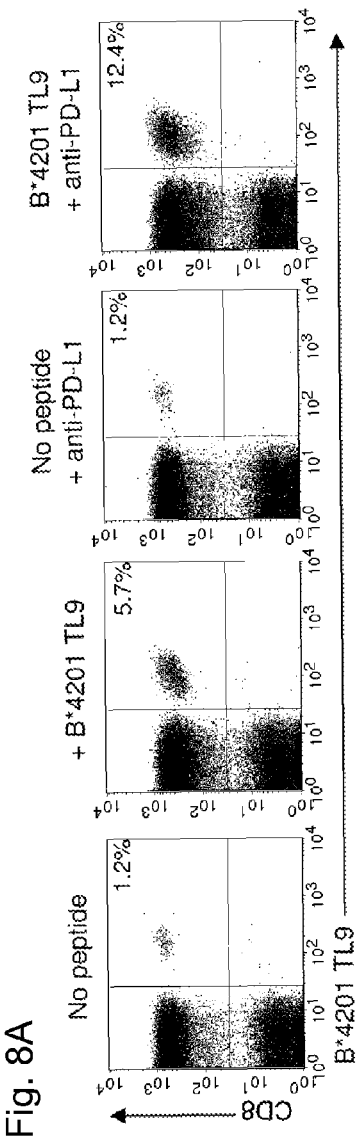
FIG. 8A is a series of images of a flow cytometry experiment showing the representative proliferation assay data from a B*4201 positive subject. After a 6-day stimulation with peptide, the percentage of B*4201 TL9-specific CD8 T cells increased from 5.7% to 12.4% in the presence of anti-PD-L1 blocking antibody.
Figure 8C:
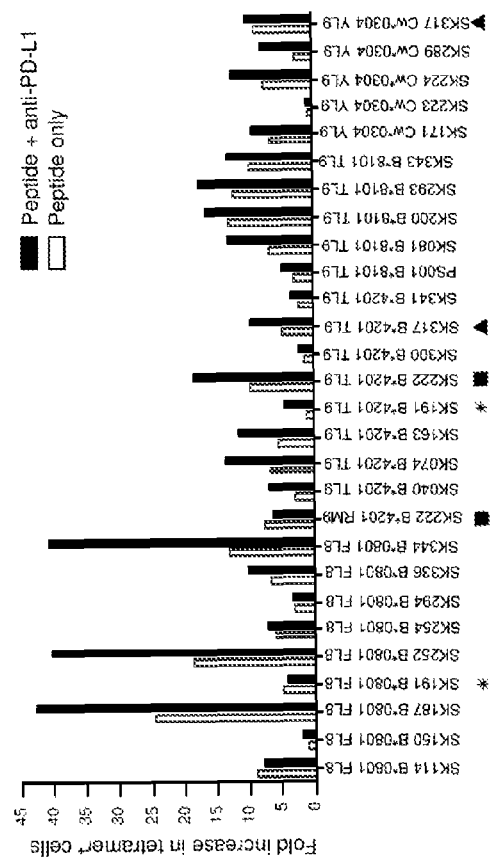
FIG. 8C is a bar graph showing the differential effects of PD-1/PD-L1 blockade on proliferation of HIV-specific CD8 T cells on an individual patient basis. White bars indicate fold increase of tetramer+ cells in the presence of peptide alone, black bars indicate the fold increase of tetramer+ cells in the presence of peptide plus anti-PD-L1 blocking antibody. Individuals in whom CFSE assays were performed for more than one epitope are indicated by asterisk, square, or triangle symbols.
Figure 8B:
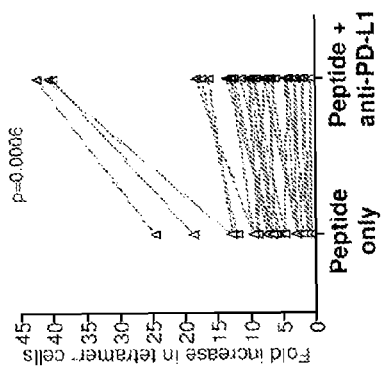
FIG. 8B is a line graph depicting the summary proliferation assay data indicating a significant increase in proliferation of HIV-specific CD8 T cells in the presence of anti-PD-L1 blocking antibody (n=28, p=0.0006, paired t-test).

Effect of Blockading the PD-1/PD-L1 Pathway on Proliferation of HIV-Specific CD8 T Cells Because HIV-specific CD8 T cells also exhibit impaired proliferative capacity (Migueles S A, et al. 2002; Lichterfeld M, et al. 2004), it was determined whether blockade of the PD-1/PD-L1 could enhance this function in vitro. Representative data from a B*4201-positive individual are shown in FIG. 8A. Incubation of freshly isolated CFSE-labeled PBMC with medium alone, or medium with anti-PD-L1 antibody, resulted in maintenance of a population of B*4201-TL9-specific CD8 T cells (1.2% of CD8 T cells) that remained CFSE$^{hi}$ after six days in culture. Simulation of CFSE-labeled PBMC for 6 days with TL9 peptide alone resulted in a 4.8-fold expansion of CFSE$^{lo}$ B*4201 TL9 tetramer$^+$ cells, whereas stimulation of CFSE-labeled PBMC with TL9 peptide in the presence of anti-PD-L1 blocking antibody further enhanced proliferation of TL9-specific cells, resulting in a 10.3-fold increase in tetramer$^+$ cells. CFSE proliferation assays were performed on 28 samples in the presence and absence of purified anti-human PD-L1 blocking antibody. A significant increase in the proliferation of HIV-specific CD8$^+$ T cells was observed in the presence of peptide plus anti-PD-L1 blocking antibody as compared to the amount of proliferation following stimulation with peptide alone (FIG. 8B; p=0.0006, paired t-test). The fold increase of tetramer$^+$ cells in the presence of anti-PD-L1 blocking antibody varied by individual and by epitope within a given individual (FIG. 8C), again suggesting epitope-specific differences in the degree of functional exhaustion of these responses.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of increasing cytotoxic activity of anergic T cells in a subject having a lymphoproliferative cancer, comprising
administering to the subject having the lymphoproliferative cancer an effective amount of an agent that reduces the activity or expression of a Programmed Cell Death (PD)-1 polypeptide, wherein the agent is an anti-Programmed Cell Death Ligand (PD-L)1 antibody,
thereby increasing the cytotoxic activity of anergic T cells in the subject with the lymphoproliferative cancer, wherein the lymphoproliferative cancer is a Hodgkin's lymphoma.

2. The method of claim 1, wherein increasing the cytotoxic activity of anergic T cells comprises increasing cytokine production or T cell proliferation.

3. The method of claim 2, wherein the cytokine is interferon γ, tumor necrosis factor α or interleukin-2.

4. The method of claim 1, further comprising measuring cytotoxic T cell activity in a biological sample from the subject.

5. The method of claim 4, wherein measuring cytotoxic T cell activity comprises measuring the cytotoxic activity of anergic CD8+ T cells in the biological sample from the subject.

6. The method of claim 4, wherein measuring cytotoxic T cell activity comprises measuring the production of a cytokine by T cells in the biological sample from the subject.

7. The method of claim 6, wherein the cytokine is interferon γ, tumor necrosis factor α or interleukin-2.

8. The method of claim 1, wherein the Hodgkin's lymphoma is a nodular lymphocyte predominant Hodgkin's lymphoma.

9. The method of claim 1, wherein the method further comprises administering to the subject an effective amount of a second compound that induces an immune response.

10. The compound of claim 9, wherein the second compound is an anti-inflammatory compound, an antineoplastic compound or an analgesic.

11. The method of claim 9, wherein the second compound is an anti-CTLA-4 antibody, an anti-BTLA antibody, an anti-B7-H4 antibody.

12. The method of claim 9, wherein the second compound reduces cancer cell volume.

13. The method of claim 1, wherein the antibody is a monoclonal antibody, a humanized antibody, a deimmunized antibody, or an immunoglobulin (Ig) fusion protein.

14. The method of claim 1, wherein the subject is human.

15. The method of claim 1, wherein the method decreases a symptom of the lymphoproliferative cancer in the subject.

16. The method of claim 1, wherein the method decreases the size of the tumor or the prevalence of cancer cells.

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic HIV MHC Class I peptide.

```
<400> SEQUENCE: 1

Gly Ala Phe Asp Leu Ser Phe Phe Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 2

Lys Ile Gln Asn Phe Arg Val Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic HIV MHC Class I peptide.

<400> SEQUENCE: 3

Asp Ile Tyr Lys Arg Trp Ile Ile
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic HIV MHC Class I peptide.

<400> SEQUENCE: 4

Phe Leu Lys Glu Lys Gly Gly Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 5

Arg Pro Gln Val Pro Leu Arg Pro Met
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 6

Thr Pro Gln Asp Leu Asn Thr Met Leu
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic HIV MHC Class I peptide.
```

```
<400> SEQUENCE: 7

Thr Pro Gly Pro Gly Val Arg Tyr Pro Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 8

Tyr Pro Gly Ile Lys Val Lys Gln Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 9

Thr Pro Gln Asp Leu Asn Thr Met Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic HIV MHC Class I peptide.

<400> SEQUENCE: 10

Tyr Val Asp Arg Phe Phe Lys Thr Leu
1               5
```